US007511188B2

(12) United States Patent
Ali et al.

(10) Patent No.: US 7,511,188 B2
(45) Date of Patent: Mar. 31, 2009

(54) METHODS OF PROTECTING PLANTS FROM PATHOGENIC FUNGI

(75) Inventors: Hana S. Ali, San Francisco, CA (US);
Robert J. Keenan, Chicago, IL (US);
Michael Lassner, Foster City, CA (US);
Mathias L. Muller, Santa Cruz, CA (US); Gusui Wu, Palo Alto, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/956,384

(22) Filed: Dec. 14, 2007

(65) Prior Publication Data

US 2008/0120743 A1 May 22, 2008

Related U.S. Application Data

(62) Division of application No. 11/172,571, filed on Jun. 30, 2005, now Pat. No. 7,332,650.

(60) Provisional application No. 60/584,905, filed on Jun. 30, 2004.

(51) Int. Cl.
C12N 15/09 (2006.01)
C12N 15/82 (2006.01)
A01H 5/00 (2006.01)
A01H 5/10 (2006.01)

(52) U.S. Cl. .................. 800/279; 800/278; 800/298; 800/295; 800/320.1; 800/317; 435/468

(58) Field of Classification Search ................ None
See application file for complete search history.

(56) References Cited

U.S. PATENT DOCUMENTS 6,187,904 B1 2/2001 Broekaert et al.

FOREIGN PATENT DOCUMENTS

WO WO 93/05153 3/1993

OTHER PUBLICATIONS

Terras, et. al., A new family of basic cysteine-rich plant antifungal proteins from Brassicaceae species, FEBS, (1993), 316(3):233-240.
Choi, et al., Nucleotide Sequence of a cDNA Encoding a Low Molecular Weight Sulfur-Rich Protein in Soybean Seeds, Plant Physiol., (1993), 101:699-700.
Milligan, et al., Nature and regulation of pistil-expressed genes in tomato, Plant Mol. Biol., (1995), 28(4):691-711.
Yamada, et al., cDNA cloning of gamma-thionin from *Nicotiana excelsior*, NCBI, (1997), Accession BAA21113.
Zhang, et al., Fabatins: new antimicrobial plant peptides, FEMS Microbiology Letters, (1997), 149:59-64.
Lopez, et al., Sequences of ndhA gene of barley (*Hordeum vulgare* L.) plastid (accession Nos. Y13729 and Y13730), Plant Physiol. (1997), 115:313-315.

Aluru, et al., Nucleotide sequence of a defensin or gamma-thionin-like gene (Accession No. AF128239) from habanero chile (PGR 99-070), NCBI, (1999), Accession AAD21200.
Aluru, et al., Nucleotide sequence of a defensin or gamma-thionin-like gene (Accession No. AF128239) from habanero chile (PGR 99-070), NCBI, (1999), Accession AF128239.
Sinisterra, et al., Expression of Proteinase inhibitor SE60 homolog in grapefruit flavedo, NCBI (2000), Accession AAG38520.
Urdangarin, et al., A defensin gene expressed in sunflower inflorescence, NCBI, (2000), Accession AAF72043.
Urdangarin, et al., Cloning of defensin cDNA expressed in sunflower (*Helianthus annuus*) inflorescence, NCBI, (2000), Accession AAF66592.
Yun, et al., NCBI, (2000), Accession T02667.
Kim, et al., NCBI (2000), Accession T14395.
Cushman, et al., NCBI, (2000), Accession T06381.
Takemoto, et al., NCBI, (2000), Accession BAA95697.
Choi, et al., Tissue-specific and developmental regulation of a gene encoding a low molecular weight sulfur-rich protein in soybean seeds, NCBI, (2000), Accession S51637.
Weterings, et al., NCBI, (2000), Accession AAG17880.
Sharma, et al., NCBI, (2000), Accession T14866.
Heck, et al., Gibberellin-repressible gene expression in the barley aleurone layer, NCBI, (2000), Accession S65779.
Brandstadter, et al., Expression of genes for a defensin and a proteinase inhibitor in specific areas of the shoot apex and the developing flower in tomato, NCBI, (2000), Accession S57809.
Van Der Hoeven, et al., Generation of ESTs from tomato flower tissue, 3-8 mm buds, NCBI, (2001), Accession BI927975.
Van Der Hoeven, et al., Generation of ESTs from Tomato Suspension Cultures, NCBI, (2001), Accession BI205125.
Fils-Lycaon, et al., NCBI, (2001), Accession AAL14240.
Chen, et al., A Novel Defensin Encoded by a Mungbean cDNA Exhibits Insecticidal Activity against Bruchid, J. Agric. Food Chem., (2002), 50:7258-7263.
Zhou, et al., NCBI, (2002), Accession BAB64929.
Schafleitner, et al., NCBI, (2003), Accession AAL15885.
Do, et al., Differential expression and in situ localization of a pepper defensin (CADEF1) gene in response to pathogen infection, abiotic elicitors and environmental stresses in *Capsicum annuum*, NCBI, (2004), Accession No. AAL35366.
Bloch, et al., A new family of small (5 kDa) protein inhibitors of insect alpha-amylases from seeds or sorghum (*Sorghum bicolar* (L) Moench) have sequence homologies with wheat gamma-purothionins, NCBI, (2004), Accession P21925.
Lee, et al., Pepper gene encoding thionin is differentially induced by pathogens, ethylene and methyl jasmonate, NCBI, (2004), Accession AAF18936.
Sasaki, et al., The genome sequence and structure of rice chromosome 1, NCBI, (2004), Accession BAB67948.

(Continued)

*Primary Examiner*—Medina A Ibrahim

(57) ABSTRACT

Methods for protecting a plant from a plant pathogenic fungus are provided. A method for enhancing fungal pathogen resistance in a plant using the nucleotide sequences disclosed herein is further provided. The method comprises introducing into a plant an expression cassette comprising a promoter operably linked to a nucleotide sequence that encodes an antifungal polypeptide of the invention. Transformed plants, plant cells, seeds, and microorganisms comprising a nucleotide sequence that encodes an antifungal polypeptide of the embodiments, or variant or fragment thereof, are also disclosed.

19 Claims, No Drawings

OTHER PUBLICATIONS

Bloch, et al., A new family of small (5 kDa) protein inhibitors of insect alpha-amylases from seeds or sorghum (*Sorghum bicolar* (L) Moench) have sequence homologies with wheat gamma-purothionins, NCBI, (2004), Accession P21924.

Terras, et al., Small cysteine-rich antifungal proteins from radish: their role in host defense, NCBI, (2004), Accession P30225.

Zhang, et al., Fabatins: new antimicrobial plant peptides, NCBI, (2005), Accession P81456.

Chen, et al., A novel defensin encoded by a mungbean cDNA exhibits insecticidal activity against bruchid, NCBI, (2005), Accession AAG45227.

Kragh, et al., Characterization and localization of new antifungal cysteine-rich proteins from Beta vulgaris, NCBI, (2005), Accession P81493.

NCBI, (2005), Accession NP_178322.

Kragh, et al., Characterization and localization of new antifungal cysteine-rich proteins from Beta vulgaris, NCBI, (2005), Accession P82010.

NCBI, (2005), Accession NP_178321.

Meyer, B., NCBI, (2005), Accession CAA65045.

NCBI, (2005), Accession NP_176302.

Van Den Heuvel, et al., NCBI, (2005), Accession CAB42006.

NCBI, (2005), Accession NP_178319.

NCBI, (2005), Accession NP_201171.

NCBI, (2005), Accession NP_178320.

Colilla, et al., gamma-Purothionins: amino acid sequence of two polypeptides of a new family of thionins from wheat endosperm, NCBI, (2005), Accession P20159.

Mendez, et al., Primary structure and inhibition of protein synthesis in eukaryotic cell-free system of a novel thionin, gamma-hordothionin, from barley endosperm, NCBI, (2005), Accession P20230.

Colilla, et al., gamma-Purothionins: amino acid sequence of two polypeptides of a new family of thionins from wheat endosperm, NCBI, (2005), P20158.

Castro, et al., Complete amino acid sequences of two gamma-thionins from maize (*Zea mays* L.) seeds, NCBI, (2005), Accession P81008.

NCBI, (2005), Accession NP_180171.

Meyer, et al., Fruit-specific expression of a defensin-type gene family in bell pepper. Upregulation during ripening and upon wounding, NCBI, (2006), Accession O65740.

Stiekema, et al., Molecular cloning and analysis of four potato tuber mRNAs, NCBI, (2006), Accession P20346.

Urdangarin, et al., A defensin gene expressed in sunflower inflorescence, NCBI, (2006), Accession P82659.

Gu, et al., A flower-specific cDNA encoding a novel thionin in tobacco, NCBI, (2006), Accession P32026.

Karunanandaa, et al., Characterization of a predominantly pistil-expressed gene encoding a gamma-thionin-like protein of Petunia inflate, NCBI, (2006), Accession Q40901.

Meyer, et al., Fruit-specific expression of a defensin-type gene family in bell pepper. Upregulation during ripening and upon wounding, NCBI, (2006), Accession Q43413.

Choi, et al., Nucleotide sequence of a cDNA encoding a low molecular weight sulfur-rich protein in soybean seeds, NCBI, (2006), Accession Q07502.

Komori, et al., A cDNA clone for gamma-thionin from *Nicotiana paniculata*, NCBI, (2006), Accession O24115.

Johnson, et al., Novel insecticidal peptides from *Tegenaria agrestis* spider venom may have a direct effect on the insect central nervous system, NCBI, (2006), Accession O46167.

Thevissen, et al., Interactions of antifungal plant defensins with fungal membrane components, Peptides, (2003), 24:1705-1712.

Thomma, et al., Plant Defensins, Planta, (2002), 216:193-202.

Punja, Zamir K., Genetic engineering of plants to enhance resistance to fungal pathogens-a review of progress and future prospects. J. Plant Pathol., (2001), 23:216-235.

Gao, et al., Fungal pathogen protection in potato by expression of a plant defensin peptide, Nature Biotechnology, (2000), 18(12):1307-1310.

Lai, et al., Analysis of the DRR230 family of pea defensins: gene expression pattern and evidence of broad host-range antifungal activity. Plant Science, (2002), 163:855-864.

Horvath, et al., Gentically engineered stem rust resistance in barley using the Rpg1 gene, PNAS (2003), 100(1): 364-369.

Lorito, et al.., Genes from mycoparasitic fungi as a source for improving plant resistance to fungal pathogens, PNAS, (1998), 95(14): 7860-7865.

Lazar, et al., , Molecular and Cellular Biology, Mar. 1988, 8(3): 1247-1257.

Broun et al., Science, Nov. 13, 1998, 282: 1315-1317.

United States Patent US 7,511,188 B2

SEQUENCE LISTING

```
<160> NUMBER OF SEQ ID NOS: 78

<210> SEQ ID NO 1
<211> LENGTH: 80
<212> TYPE: PRT
<213> ORGANISM: Brassica napus
<220> FEATURE:
<221> NAME/KEY: PEPTIDE
<222> LOCATION: (0)...(0)
<223> OTHER INFORMATION: Dfn2 (P30225)

<400> SEQUENCE: 1

Met Ala Lys Phe Ala Ser Ile Ile Ala Leu Leu Phe Ala Ala Leu Val
1               5                   10                  15

Leu Phe Ala Ala Phe Glu Ala Pro Thr Met Val Glu Ala Gln Lys Leu
20                  25                  30

Cys Glu Arg Pro Ser Gly Thr Trp Ser Gly Val Cys Gly Asn Asn Asn
35                  40                  45

Ala Cys Lys Asn Gln Cys Ile Asn Leu Glu Lys Ala Arg His Gly Ser
50                  55                  60

Cys Asn Tyr Val Phe Pro Ala His Lys Cys Ile Cys Tyr Phe Pro Cys
65                  70                  75                  80

<210> SEQ ID NO 2
<211> LENGTH: 51
<212> TYPE: PRT
<213> ORGANISM: Brassica napus
<220> FEATURE:
<221> NAME/KEY: PEPTIDE
<222> LOCATION: (0)...(0)
<223> OTHER INFORMATION: Dfn2  mature sequence

<400> SEQUENCE: 2

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn Leu Glu Lys Ala Arg
20                  25                  30

His Gly Ser Cys Asn Tyr Val Phe Pro Ala His Lys Cys Ile Cys Tyr
35                  40                  45

Phe Pro Cys
50

<210> SEQ ID NO 3
```

<211> LENGTH: 153
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence Encoding SEQ ID NO:2 as expressed in E. coli for anti-fungal bioassays
<221> NAME/KEY: CDS
<222> LOCATION: (1)...(153)

<400> SEQUENCE: 3

```
cag aaa ctg tgc gaa cgt ccg agc ggt act tgg agc ggc gtt tgc ggt      48
Gln Lys Leu Cys Glu Arg Pro Ser Gly Thr Trp Ser Gly Val Cys Gly
1               5                   10                  15 aac aac aac gcg tgc aag aac caa tgc atc aac ctg gaa aag gct cgc      96
Asn Asn Asn Ala Cys Lys Asn Gln Cys Ile Asn Leu Glu Lys Ala Arg
            20                  25                  30 cac ggt tct tgc aac tac gta ttc ccg gcc cac aaa tgc atc tgc tat     144
His Gly Ser Cys Asn Tyr Val Phe Pro Ala His Lys Cys Ile Cys Tyr
        35                  40                  45 ttc ccg tgc                                                         153
Phe Pro Cys
50
```

<210> SEQ ID NO 4
<211> LENGTH: 80
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: Dfn 4 (NP_180171)

<400> SEQUENCE: 4

```
Met Ala Lys Ser Ala Ala Ile Ile Thr Phe Leu Phe Ala Ala Leu Val
1               5                   10                  15

Leu Phe Ala Ala Phe Glu Ala Pro Ile Met Val Glu Ala Gln Lys Leu
            20                  25                  30

Cys Glu Lys Pro Ser Gly Thr Trp Ser Gly Val Cys Gly Asn Ser Asn
        35                  40                  45

Ala Cys Lys Asn Gln Cys Ile Asn Leu Glu Gly Ala Lys His Gly Ser
    50                  55                  60

Cys Asn Tyr Val Phe Pro Ala His Lys Cys Ile Cys Tyr Phe Pro Cys
65                  70                  75                  80
```

<210> SEQ ID NO 5
<211> LENGTH: 50
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: Dfn4 mature sequence

<400> SEQUENCE: 5

```
Lys Leu Cys Glu Lys Pro Ser Gly Thr Trp Ser Gly Val Cys Gly Asn
1               5                   10                  15

Ser Asn Ala Cys Lys Asn Gln Cys Ile Asn Leu Glu Gly Ala Lys His
            20                  25                  30

Gly Ser Cys Asn Tyr Val Phe Pro Ala His Lys Cys Ile Cys Tyr Phe
        35                  40                  45

Pro Cys
```

```
<210> SEQ ID NO 6
<211> LENGTH: 150
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:5 as expressed in
      E. coli for anti-fungal bioassays
<221> NAME/KEY: CDS
<222> LOCATION: (1)...(150)

<400> SEQUENCE: 6 aaa ctg tgt gaa aaa cca tcc ggt acc tgg tcc ggt gtt tgt ggc aac      48
Lys Leu Cys Glu Lys Pro Ser Gly Thr Trp Ser Gly Val Cys Gly Asn
1               5                   10                  15 tcc aac gct tgt aaa aac cag tgt atc aat ctg gaa ggt gcg aaa cac      96
Ser Asn Ala Cys Lys Asn Gln Cys Ile Asn Leu Glu Gly Ala Lys His
            20                  25                  30 ggc tcc tgt aac tac gta ttt ccg gcg cac aaa tgt atc tgc tac ttc     144
Gly Ser Cys Asn Tyr Val Phe Pro Ala His Lys Cys Ile Cys Tyr Phe
        35                  40                  45 cct tgt                                                              150
Pro Cys
50

<210> SEQ ID NO 7
<211> LENGTH: 73
<212> TYPE: PRT
<213> ORGANISM: Vigna radiata
<220> FEATURE:
<221> NAME/KEY: PEPTIDE
<222> LOCATION: (0)...(0)
<223> OTHER INFORMATION: Dfn7 (AAG45227)

<400> SEQUENCE: 7

Met Glu Arg Lys Thr Phe Ser Phe Leu Phe Ser Leu Leu Leu Val Leu
1               5                   10                  15

Ala Ser Asp Val Ala Val Glu Arg Gly Glu Ala Arg Thr Cys Met Ile
            20                  25                  30

Lys Lys Glu Gly Trp Gly Lys Cys Leu Ile Asp Thr Thr Cys Ala His
        35                  40                  45

Ser Cys Lys Asn Arg Gly Tyr Ile Gly Gly Asp Cys Lys Gly Met Thr
    50                  55                  60

Arg Thr Cys Tyr Cys Leu Val Asn Cys
65                  70

<210> SEQ ID NO 8
<211> LENGTH: 46
<212> TYPE: PRT
<213> ORGANISM: Vigna radiata
<220> FEATURE:
<221> NAME/KEY: PEPTIDE
<222> LOCATION: (0)...(0)
<223> OTHER INFORMATION: Dfn7 mature sequence

<400> SEQUENCE: 8

Arg Thr Cys Met Ile Lys Lys Glu Gly Trp Gly Lys Cys Leu Ile Asp
1               5                   10                  15

Thr Thr Cys Ala His Ser Cys Lys Asn Arg Gly Tyr Ile Gly Gly Asp
            20                  25                  30
```

```
Cys Lys Gly Met Thr Arg Thr Cys Tyr Cys Leu Val Asn Cys
 35              40                  45
```

<210> SEQ ID NO 9
<211> LENGTH: 138
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:8 as expressed in
      E. coli for anti-fungal bioassays
<221> NAME/KEY: CDS
<222> LOCATION: (1)...(138)

<400> SEQUENCE: 9

```
cgc acc tgt atg att aag aaa gaa ggt tgg ggc aaa tgc ctg atc gat         48
Arg Thr Cys Met Ile Lys Lys Glu Gly Trp Gly Lys Cys Leu Ile Asp
1               5                   10                  15 act acc tgt gcg cat tct tgt aaa aac cgt ggc tac atc ggc ggt gat         96
Thr Thr Cys Ala His Ser Cys Lys Asn Arg Gly Tyr Ile Gly Gly Asp
            20                  25                  30 tgt aaa ggt atg acg cgc act tgt tac tgt ctg gtt aat tgc                138
Cys Lys Gly Met Thr Arg Thr Cys Tyr Cys Leu Val Asn Cys
 35              40                  45
```

<210> SEQ ID NO 10
<211> LENGTH: 47
<212> TYPE: PRT
<213> ORGANISM: Vicia faba
<220> FEATURE:
<221> NAME/KEY: PEPTIDE
<222> LOCATION: (0)...(0)
<223> OTHER INFORMATION: Dfn9 (P81456)

<400> SEQUENCE: 10

```
Leu Leu Gly Arg Cys Lys Val Lys Ser Asn Arg Phe His Gly Pro Cys
1               5                   10                  15

Leu Thr Asp Thr His Cys Ser Thr Val Cys Arg Gly Glu Gly Tyr Lys
            20                  25                  30

Gly Gly Asp Cys His Gly Leu Arg Arg Arg Cys Met Cys Leu Cys
 35              40                  45
```

<210> SEQ ID NO 11
<211> LENGTH: 44
<212> TYPE: PRT
<213> ORGANISM: Vicia faba
<220> FEATURE:
<221> NAME/KEY: PEPTIDE
<222> LOCATION: (0)...(0)
<223> OTHER INFORMATION: Dfn9 mature peptide

<400> SEQUENCE: 11

```
Arg Cys Lys Val Lys Ser Asn Arg Phe His Gly Pro Cys Leu Thr Asp
1               5                   10                  15

Thr His Cys Ser Thr Val Cys Arg Gly Glu Gly Tyr Lys Gly Gly Asp
            20                  25                  30

Cys His Gly Leu Arg Arg Arg Cys Met Cys Leu Cys
 35              40
```

<210> SEQ ID NO 12
<211> LENGTH: 132
<212> TYPE: DNA
<213> ORGANISM: Artificial Sequence
<220> FEATURE:

<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:11 as expressed in
      E. coli for anti-fungal bioassays
<221> NAME/KEY: CDS
<222> LOCATION: (1)...(132)

<400> SEQUENCE: 12

```
cgc tgt aag gtc aaa tct aac cgt ttt cac ggc ccg tgc ctg acg gat      48
Arg Cys Lys Val Lys Ser Asn Arg Phe His Gly Pro Cys Leu Thr Asp
1               5                  10                  15 act cat tgt agc acc gtg tgt cgt ggc gag ggc tac aaa ggc ggt gat      96
Thr His Cys Ser Thr Val Cys Arg Gly Glu Gly Tyr Lys Gly Gly Asp
            20                  25                  30 tgt cac ggt ctg cgt cgc cgc tgt atg tgt ctg tgt                     132
Cys His Gly Leu Arg Arg Arg Cys Met Cys Leu Cys
        35                  40
```

<210> SEQ ID NO 13
<211> LENGTH: 79
<212> TYPE: PRT
<213> ORGANISM: Nicotiana excelsior
<220> FEATURE:
<221> NAME/KEY: PEPTIDE
<222> LOCATION: (0)...(0)
<223> OTHER INFORMATION: Dfn 13 (BAA21113)

<400> SEQUENCE: 13

```
Leu Phe Val Ala Tyr Glu Val Gln Ala Arg Glu Cys Ala Arg Glu Ile
1               5                  10                  15

Phe Thr Gly Leu Cys Ile Thr Asn Pro Gln Cys Arg Lys Ala Cys Ile
            20                  25                  30

Lys Glu Lys Phe Thr Asp Gly His Cys Ser Lys Ile Leu Arg Arg Cys
        35                  40                  45

Leu Cys Thr Lys Pro Cys Thr Gly Ala Glu Thr Leu Ala Glu Glu Ala
    50                  55                  60

Thr Thr Leu Ala Ala Ala Leu Leu Glu Glu Glu Ile Met Asp Asn
65                  70                  75
```

<210> SEQ ID NO 14
<211> LENGTH: 45
<212> TYPE: PRT
<213> ORGANISM: Nicotiana excelsior
<220> FEATURE:
<221> NAME/KEY: PEPTIDE
<222> LOCATION: (0)...(0)
<223> OTHER INFORMATION: Dfn13 mature peptide

<400> SEQUENCE: 14

```
Arg Glu Cys Ala Arg Glu Ile Phe Thr Gly Leu Cys Ile Thr Asn Pro
1               5                  10                  15

Gln Cys Arg Lys Ala Cys Ile Lys Glu Lys Phe Thr Asp Gly His Cys
            20                  25                  30

Ser Lys Ile Leu Arg Arg Cys Leu Cys Thr Lys Pro Cys
        35                  40                  45
```

<210> SEQ ID NO 15
<211> LENGTH: 135
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)

<223> OTHER INFORMATION: Sequence encoding SEQ ID NO:14 as expressed in
      E. coli for anti-fungal bioassays
<221> NAME/KEY: CDS
<222> LOCATION: (1)...(135)

<400> SEQUENCE: 15

```
cgc gag tgt gca cgt gaa atc ttc acc ggt ctg tgc atc act aac cca      48
Arg Glu Cys Ala Arg Glu Ile Phe Thr Gly Leu Cys Ile Thr Asn Pro
1               5                   10                  15 cag tgc cgc aaa gca tgc att aaa gaa aaa ttc act gac ggc cac tgt      96
Gln Cys Arg Lys Ala Cys Ile Lys Glu Lys Phe Thr Asp Gly His Cys
            20                  25                  30 tct aaa att ctg cgt cgc tgt ctg tgc act aaa ccg tgc                  135
Ser Lys Ile Leu Arg Arg Cys Leu Cys Thr Lys Pro Cys
35                  40                  45
```

<210> SEQ ID NO 16
<211> LENGTH: 49
<212> TYPE: PRT
<213> ORGANISM: Musa acuminata
<220> FEATURE:
<221> NAME/KEY: PEPTIDE
<222> LOCATION: (0)...(0)
<223> OTHER INFORMATION: Dfn14 (AAL14240)

<400> SEQUENCE: 16

```
Glu Ser Arg Thr Cys Glu Ser Ala Ser Thr Arg Phe Lys Gly Thr Cys
1               5                   10                  15

Val Arg Ser Ser Asn Cys Ala Ser Val Cys Gln Gly Glu Gly Phe Pro
            20                  25                  30

Asp Gly Lys Cys Glu Gly Val Arg Arg Arg Cys Met Cys Arg Lys Pro
35                  40                  45

Cys
```

<210> SEQ ID NO 17
<211> LENGTH: 47
<212> TYPE: PRT
<213> ORGANISM: Musa acuminata
<220> FEATURE:
<221> NAME/KEY: PEPTIDE
<222> LOCATION: (0)...(0)
<223> OTHER INFORMATION: Dfn14 mature peptide

<400> SEQUENCE: 17

```
Arg Thr Cys Glu Ser Ala Ser Thr Arg Phe Lys Gly Thr Cys Val Arg
1               5                   10                  15

Ser Ser Asn Cys Ala Ser Val Cys Gln Gly Glu Gly Phe Pro Asp Gly
            20                  25                  30

Lys Cys Glu Gly Val Arg Arg Arg Cys Met Cys Arg Lys Pro Cys
35                  40                  45
```

<210> SEQ ID NO 18
<211> LENGTH: 141
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:17 as expressed in
      E. coli for anti-fungal bioassays
<221> NAME/KEY: CDS
<222> LOCATION: (1)...(141)

<400> SEQUENCE: 18

```
cgc acc tgt gaa tct gca tcc act cgt ttt aaa ggt acc tgt gtc cgt    48
Arg Thr Cys Glu Ser Ala Ser Thr Arg Phe Lys Gly Thr Cys Val Arg
1               5                   10                  15 tcc tcc aac tgt gca tct gtt tgt cag ggc gaa ggc ttc ccg gac ggc    96
Ser Ser Asn Cys Ala Ser Val Cys Gln Gly Glu Gly Phe Pro Asp Gly
      20                  25                  30 aaa tgt gaa ggc gtg cgc cgc cgc tgc atg tgt cgt aaa ccg tgc       141
Lys Cys Glu Gly Val Arg Arg Arg Cys Met Cys Arg Lys Pro Cys
35                  40                  45
```

<210> SEQ ID NO 19
<211> LENGTH: 74
<212> TYPE: PRT
<213> ORGANISM: Glycine max
<220> FEATURE:
<221> NAME/KEY: PEPTIDE
<222> LOCATION: (0)...(0)
<223> OTHER INFORMATION: Dfn16 (Q07502)

<400> SEQUENCE: 19

```
Met Glu Met Arg Lys Ser Cys Gly Phe Phe Leu Leu Leu Leu Leu
1               5                   10                  15

Val Phe Ala Ser Gln Val Val Val Gln Thr Glu Gly Arg Val Cys Glu
            20                  25                  30

Ser Gln Ser His Gly Phe His Gly Leu Cys Asn Arg Asp His Asn Cys
35                  40                  45

Ala Leu Val Cys Arg Asn Glu Gly Phe Ser Gly Gly Arg Cys Lys Arg
50                  55                  60

Ser Arg Arg Cys Phe Cys Thr Arg Ile Cys
65                  70
```

<210> SEQ ID NO 20
<211> LENGTH: 46
<212> TYPE: PRT
<213> ORGANISM: Glycine max
<220> FEATURE:
<221> NAME/KEY: PEPTIDE
<222> LOCATION: (0)...(0)
<223> OTHER INFORMATION: Dfn16 mature peptide

<400> SEQUENCE: 20

```
Arg Val Cys Glu Ser Gln Ser His Gly Phe His Gly Leu Cys Asn Arg
1               5                   10                  15

Asp His Asn Cys Ala Leu Val Cys Arg Asn Glu Gly Phe Ser Gly Gly
            20                  25                  30

Arg Cys Lys Arg Ser Arg Arg Cys Phe Cys Thr Arg Ile Cys
35                  40                  45
```

<210> SEQ ID NO 21
<211> LENGTH: 138
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:20 as expressed in
      E. coli for anti-fungal bioassays
<221> NAME/KEY: CDS
<222> LOCATION: (1)...(138)

<400> SEQUENCE: 21

```
cgc gtg tgt gaa tct caa tcc cac ggt ttt cac ggt ctg tgt aac cgt    48
Arg Val Cys Glu Ser Gln Ser His Gly Phe His Gly Leu Cys Asn Arg
1               5                   10                  15
```

```
gac cat aac tgt gca ctg gtt tgt cgt aat gaa ggc ttc tct ggt ggc      96
Asp His Asn Cys Ala Leu Val Cys Arg Asn Glu Gly Phe Ser Gly Gly
 20                  25                  30 cgt tgt aag cgt tct cgc cgc tgt ttc tgt acc cgt atc tgc              138
Arg Cys Lys Arg Ser Arg Arg Cys Phe Cys Thr Arg Ile Cys
 35                  40                  45

<210> SEQ ID NO 22
<211> LENGTH: 73
<212> TYPE: PRT
<213> ORGANISM: Citrus x paradisi
<220> FEATURE:
<221> NAME/KEY: PEPTIDE
<222> LOCATION: (0)...(0)
<223> OTHER INFORMATION: Dfn25 (AAG38520)

<400> SEQUENCE: 22

Met Lys Ser Phe Phe Gly Ile Phe Leu Leu Leu Ile Leu Phe Ala
 1               5                  10                  15

Ser Gln Glu Ile Met Val Pro Ala Glu Gly Arg Val Cys Gln Ser Gln
 20                  25                  30

Ser His His Phe His Gly Ala Cys Phe Ser His Asn Cys Ala Phe
 35                  40                  45

Val Cys Arg Asn Glu Gly Phe Ser Gly Gly Lys Cys Arg Gly Val Arg
 50                  55                  60

Arg Arg Cys Phe Cys Ser Lys Leu Cys
 65                  70

<210> SEQ ID NO 23
<211> LENGTH: 47
<212> TYPE: PRT
<213> ORGANISM: Citrus x paradisi
<220> FEATURE:
<221> NAME/KEY: PEPTIDE
<222> LOCATION: (0)...(0)
<223> OTHER INFORMATION: Dfn25 mature sequence

<400> SEQUENCE: 23

Arg Val Cys Gln Ser Gln Ser His His Phe His Gly Ala Cys Phe Ser
 1               5                  10                  15

His His Asn Cys Ala Phe Val Cys Arg Asn Glu Gly Phe Ser Gly Gly
 20                  25                  30

Lys Cys Arg Gly Val Arg Arg Arg Cys Phe Cys Ser Lys Leu Cys
 35                  40                  45

<210> SEQ ID NO 24
<211> LENGTH: 141
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:23 as expressed in
      E. coli for anti-fungal bioassays
<221> NAME/KEY: CDS
<222> LOCATION: (1)...(141)

<400> SEQUENCE: 24 cgc gtg tgt cag tct caa tcc cac cat ttt cac ggt gca tgt ttc tcc     48
Arg Val Cys Gln Ser Gln Ser His His Phe His Gly Ala Cys Phe Ser
 1               5                  10                  15 cat cat aac tgt gca ttc gtt tgt cgt aat gaa ggc ttc tct ggt ggc     96
His His Asn Cys Ala Phe Val Cys Arg Asn Glu Gly Phe Ser Gly Gly
```

```
           20                  25                  30 aaa tgt cgc ggc gtg cgc cgc cgc tgc ttc tgt tct aaa ctg tgc        141
Lys Cys Arg Gly Val Arg Arg Arg Cys Phe Cys Ser Lys Leu Cys
 35                  40                  45
```

<210> SEQ ID NO 25
<211> LENGTH: 106
<212> TYPE: PRT
<213> ORGANISM: Nicotiana paniculata
<220> FEATURE:
<221> NAME/KEY: PEPTIDE
<222> LOCATION: (0)...(0)
<223> OTHER INFORMATION: Dfn26 (O24115 )

<400> SEQUENCE: 25

```
Met Ala Arg Ser Leu Cys Phe Met Ala Phe Ala Val Leu Ala Met Met
 1               5                  10                  15

Leu Phe Val Ala Tyr Glu Val Gln Ala Lys Ser Thr Cys Lys Ala Glu
             20                  25                  30

Ser Asn Thr Phe Pro Gly Leu Cys Ile Thr Lys Pro Pro Cys Arg Lys
         35                  40                  45

Ala Cys Leu Ser Glu Lys Phe Thr Asp Gly Lys Cys Ser Lys Ile Leu
     50                  55                  60

Arg Arg Cys Ile Cys Tyr Lys Pro Cys Val Phe Asp Gly Lys Met Ile
 65                  70                  75                  80

Gln Thr Gly Ala Glu Asn Leu Ala Glu Glu Ala Glu Thr Leu Ala Ala
                 85                  90                  95

Ala Leu Leu Glu Glu Glu Met Met Asp Asn
            100                 105
```

<210> SEQ ID NO 26
<211> LENGTH: 49
<212> TYPE: PRT
<213> ORGANISM: Nicotiana paniculata
<220> FEATURE:
<221> NAME/KEY: PEPTIDE
<222> LOCATION: (0)...(0)
<223> OTHER INFORMATION: Dfn26 mature sequence

<400> SEQUENCE: 26

```
Lys Ser Thr Cys Lys Ala Glu Ser Asn Thr Phe Pro Gly Leu Cys Ile
 1               5                  10                  15

Thr Lys Pro Pro Cys Arg Lys Ala Cys Leu Ser Glu Lys Phe Thr Asp
             20                  25                  30

Gly Lys Cys Ser Lys Ile Leu Arg Arg Cys Ile Cys Tyr Lys Pro Cys
         35                  40                  45

Val
```

<210> SEQ ID NO 27
<211> LENGTH: 147
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:26 as expressed in
      E. coli for anti-fungal bioassays
<221> NAME/KEY: CDS
<222> LOCATION: (1)...(147)

<400> SEQUENCE: 27

```
aaa tct act tgc aaa gca gaa agc aac act ttc ccg ggc ctg tgc att         48
```

```
Lys Ser Thr Cys Lys Ala Glu Ser Asn Thr Phe Pro Gly Leu Cys Ile
1               5                   10                  15 act aaa ccg ccg tgc cgt aag gca tgc ctg tct gaa aaa ttc act gat       96
Thr Lys Pro Pro Cys Arg Lys Ala Cys Leu Ser Glu Lys Phe Thr Asp
 20              25                  30 ggc aaa tgt agc aaa atc ctg cgc cgc tgt att tgt tac aaa ccg tgt      144
Gly Lys Cys Ser Lys Ile Leu Arg Arg Cys Ile Cys Tyr Lys Pro Cys
 35              40                  45 gtt                                                                   147
Val
```

<210> SEQ ID NO 28
<211> LENGTH: 76
<212> TYPE: PRT
<213> ORGANISM: Lycopersicon lycopersicum
<220> FEATURE:
<221> NAME/KEY: PEPTIDE
<222> LOCATION: (0)...(0)
<223> OTHER INFORMATION: Dfn50 (Translation of BI205125)

<400> SEQUENCE: 28

```
Met Asn Thr Lys Val Ile Leu Ala Leu Leu Phe Cys Phe Leu Leu Val
1               5                   10                  15

Ala Ser Asn Glu Met Gln Val Gly Glu Ala Lys Val Cys Gln Arg Arg
 20              25                  30

Ser Lys Thr Trp Ser Gly Pro Cys Ile Asn Thr Gly Asn Cys Ser Arg
 35              40                  45

Gln Cys Lys Gln Gln Glu Asp Ala Arg Phe Gly Ala Cys His Arg Ser
 50              55                  60

Gly Phe Gly Phe Ala Cys Phe Cys Tyr Phe Lys Cys
 65              70                  75
```

<210> SEQ ID NO 29
<211> LENGTH: 51
<212> TYPE: PRT
<213> ORGANISM: Lycopersicon lycopersicum
<220> FEATURE:
<221> NAME/KEY: PEPTIDE
<222> LOCATION: (0)...(0)
<223> OTHER INFORMATION: Dfn50 mature peptide

<400> SEQUENCE: 29

```
Gln Lys Val Cys Gln Arg Arg Ser Lys Thr Trp Ser Gly Pro Cys Ile
1               5                   10                  15

Asn Thr Gly Asn Cys Ser Arg Gln Cys Lys Gln Gln Glu Asp Ala Arg
 20              25                  30

Phe Gly Ala Cys His Arg Ser Gly Phe Gly Phe Ala Cys Phe Cys Tyr
 35              40                  45

Phe Lys Cys
 50
```

<210> SEQ ID NO 30
<211> LENGTH: 153
<212> TYPE: DNA
<213> ORGANISM: Artificial Sequence
<220> FEATURE:
<223> OTHER INFORMATION: Optimized for expression in E. coli
<221> NAME/KEY: misc_feature
<222> LOCATION: (0)...(0)
<223> OTHER INFORMATION: Sequence encoding SEQ ID NO:35 as expressed in
      E. coli for anti-fungal bioassays
<221> NAME/KEY: CDS
<222> LOCATION: (1)...(153)

-continued

```
<400> SEQUENCE: 30 cag aaa gtt tgc caa cgt cgt agc aaa act tgg agc ggc cct tgc att        48
Gln Lys Val Cys Gln Arg Arg Ser Lys Thr Trp Ser Gly Pro Cys Ile
1               5                   10                  15 aac acc ggt aac tgc tct cgt caa tgc aaa cag caa gaa gac gct cgc        96
Asn Thr Gly Asn Cys Ser Arg Gln Cys Lys Gln Gln Glu Asp Ala Arg
            20                  25                  30 ttt ggt gcg tgc cac cgc tct ggt ttc ggc ttc gcc tgc ttc tgc tat       144
Phe Gly Ala Cys His Arg Ser Gly Phe Gly Phe Ala Cys Phe Cys Tyr
35                  40                  45 ttc aaa tgc                                                           153
Phe Lys Cys
50

<210> SEQ ID NO 31
<211> LENGTH: 51
<212> TYPE: PRT
<213> ORGANISM: Tegenaria agrestis
<220> FEATURE:
<221> NAME/KEY: PEPTIDE
<222> LOCATION: (0)...(0)
<223> OTHER INFORMATION: Dfn01 (TAL_TX2)

<400> SEQUENCE: 31

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
35                  40                  45

Gln Lys Gly
50

<210> SEQ ID NO 32
<211> LENGTH: 48
<212> TYPE: PRT
<213> ORGANISM: Hordeum vulgare
<220> FEATURE:
<221> NAME/KEY: PEPTIDE
<222> LOCATION: (0)...(0)
<223> OTHER INFORMATION: Dfn03 (S65779)

<400> SEQUENCE: 32

Arg Ile Cys Thr Gly Lys Ser Gln His His Ser Phe Pro Cys Phe Ser
1               5                   10                  15

Asp Lys Ser Cys Ala Arg Asn Cys Val Ser Glu His Gly Ala His Trp
            20                  25                  30

Thr Ala Gly Tyr Cys His Leu Arg Arg Cys Thr Cys Gln Arg Glu Cys
35                  40                  45

<210> SEQ ID NO 33
<211> LENGTH: 53
<212> TYPE: PRT
<213> ORGANISM: Capsicum annuum
<220> FEATURE:
<221> NAME/KEY: PEPTIDE
<222> LOCATION: (0)...(0)
<223> OTHER INFORMATION: Dfn05 (AF112869_1)

<400> SEQUENCE: 33

Gly Val Gln Gly Lys Glu Ile Cys Cys Lys Glu Leu Thr Lys Pro Val
1               5                   10                  15

Lys Cys Ser Ser Asp Pro Leu Cys Gln Lys Leu Cys Met Glu Lys Glu
```

```
                20                  25                  30

Lys Tyr Glu Asp Gly His Cys Phe Thr Ile Leu Ser Lys Cys Leu Cys
 35                  40                  45

Met Lys Arg Cys Asn
 50

<210> SEQ ID NO 34
<211> LENGTH: 46
<212> TYPE: PRT
<213> ORGANISM: Beta vulgaris
<220> FEATURE:
<221> NAME/KEY: PEPTIDE
<222> LOCATION: (0)...(0)
<223> OTHER INFORMATION: Dfn06 (AX2_BETVU)

<400> SEQUENCE: 34

Ala Thr Cys Arg Lys Pro Ser Met Tyr Phe Ser Gly Ala Cys Phe Ser
  1               5                  10                  15

Asp Thr Asn Cys Gln Lys Ala Cys Asn Arg Glu Asp Trp Pro Asn Gly
 20                  25                  30

Lys Cys Leu Val Gly Phe Lys Cys Glu Cys Gln Arg Pro Cys
 35                  40                  45

<210> SEQ ID NO 35
<211> LENGTH: 46
<212> TYPE: PRT
<213> ORGANISM: Beta vulgaris
<220> FEATURE:
<221> NAME/KEY: PEPTIDE
<222> LOCATION: (0)...(0)
<223> OTHER INFORMATION: Dfn08 (AX1_BETVU)

<400> SEQUENCE: 35

Ala Ile Cys Lys Lys Pro Ser Lys Phe Phe Lys Gly Ala Cys Gly Arg
  1               5                  10                  15

Asp Ala Asp Cys Glu Lys Ala Cys Asp Gln Glu Asn Trp Pro Gly Gly
 20                  25                  30

Val Cys Val Pro Phe Leu Arg Cys Glu Cys Gln Arg Ser Cys
 35                  40                  45

<210> SEQ ID NO 36
<211> LENGTH: 41
<212> TYPE: PRT
<213> ORGANISM: Helianthus annuus
<220> FEATURE:
<221> NAME/KEY: PEPTIDE
<222> LOCATION: (0)...(0)
<223> OTHER INFORMATION: Dfn10 (AAF66592)

<400> SEQUENCE: 36

Ser His Arg Phe Gln Gly Thr Cys Leu Ser Asp Thr Asn Cys Ala Asn
  1               5                  10                  15

Val Cys His Ser Glu Arg Phe Ser Gly Gly Lys Cys Arg Gly Phe Arg
 20                  25                  30

Arg Arg Cys Phe Cys Thr Thr His Cys
 35                  40

<210> SEQ ID NO 37
<211> LENGTH: 45
<212> TYPE: PRT
<213> ORGANISM: Arabidopsis thaliana
<220> FEATURE:
<221> NAME/KEY: PEPTIDE
<222> LOCATION: (0)...(0)
```

<223> OTHER INFORMATION: Dfn11 (NP_178322)

<400> SEQUENCE: 37

Arg Thr Cys Glu Ser Pro Ser Asn Lys Phe Gln Gly Val Cys Leu Asn
1               5                   10                  15

Ser Gln Ser Cys Ala Lys Ala Cys Pro Ser Glu Gly Phe Ser Gly Gly
        20                  25                  30

Arg Cys Ser Ser Leu Arg Cys Tyr Cys Ser Lys Ala Cys
    35                  40                  45

<210> SEQ ID NO 38
<211> LENGTH: 42
<212> TYPE: PRT
<213> ORGANISM: Helianthus annuus
<220> FEATURE:
<221> NAME/KEY: PEPTIDE
<222> LOCATION: (0)...(0)
<223> OTHER INFORMATION: Dfn12 (AAF72043)

<400> SEQUENCE: 38

Leu Ser His Ser Phe Lys Gly Thr Cys Leu Ser Asp Thr Asn Cys Ala
1               5                   10                  15

Asn Val Cys His Ser Glu Arg Phe Ser Gly Gly Lys Cys Arg Gly Phe
        20                  25                  30

Arg Arg Arg Cys Phe Cys Thr Thr His Cys
    35                  40

<210> SEQ ID NO 39
<211> LENGTH: 47
<212> TYPE: PRT
<213> ORGANISM: Hordeum vulgare
<220> FEATURE:
<221> NAME/KEY: PEPTIDE
<222> LOCATION: (0)...(0)
<223> OTHER INFORMATION: Dfn15 (THG_HORVU)

<400> SEQUENCE: 39

Arg Ile Cys Arg Arg Arg Ser Ala Gly Phe Lys Gly Pro Cys Val Ser
1               5                   10                  15

Asn Lys Asn Cys Ala Gln Val Cys Met Gln Glu Gly Trp Gly Gly Gly
        20                  25                  30

Asn Cys Asp Gly Pro Leu Arg Arg Cys Lys Cys Met Arg Arg Cys
    35                  40                  45

<210> SEQ ID NO 40
<211> LENGTH: 47
<212> TYPE: PRT
<213> ORGANISM: Zea mays
<220> FEATURE:
<221> NAME/KEY: PEPTIDE
<222> LOCATION: (0)...(0)
<223> OTHER INFORMATION: Dfn17 (THG1_MAIZE)

<400> SEQUENCE: 40

Arg Val Cys Arg Arg Arg Ser Ala Gly Phe Lys Gly Val Cys Met Ser
1               5                   10                  15

Asp His Asn Cys Ala Gln Val Cys Leu Gln Glu Gly Tyr Gly Gly Gly
        20                  25                  30

Asn Cys Asp Gly Ile Met Arg Gln Cys Lys Cys Ile Arg Gln Cys
    35                  40                  45

<210> SEQ ID NO 41
<211> LENGTH: 47

```
<212> TYPE: PRT
<213> ORGANISM: Triticum aestivum
<220> FEATURE:
<221> NAME/KEY: PEPTIDE
<222> LOCATION: (0)...(0)
<223> OTHER INFORMATION: Dfn18 (THG1_WHEAT)

<400> SEQUENCE: 41

Lys Ile Cys Arg Arg Arg Ser Ala Gly Phe Lys Gly Pro Cys Met Ser
1               5                   10                  15

Asn Lys Asn Cys Ala Gln Val Cys Gln Gln Glu Gly Trp Gly Gly Gly
            20                  25                  30

Asn Cys Asp Gly Pro Phe Arg Arg Cys Lys Cys Ile Arg Gln Cys
        35                  40                  45

<210> SEQ ID NO 42
<211> LENGTH: 47
<212> TYPE: PRT
<213> ORGANISM: Sorghum bicolol
<220> FEATURE:
<221> NAME/KEY: PEPTIDE
<222> LOCATION: (0)...(0)
<223> OTHER INFORMATION: Dfn19 (SIA3_SORBI)

<400> SEQUENCE: 42

Arg Val Cys Arg Arg Arg Ser Ala Gly Phe Lys Gly Leu Cys Met Ser
1               5                   10                  15

Asp His Asn Cys Ala Gln Val Cys Leu Gln Glu Gly Trp Gly Gly Gly
            20                  25                  30

Asn Cys Asp Gly Val Ile Arg Gln Cys Lys Cys Ile Arg Gln Cys
        35                  40                  45

<210> SEQ ID NO 43
<211> LENGTH: 47
<212> TYPE: PRT
<213> ORGANISM: Triticum aestivum
<220> FEATURE:
<221> NAME/KEY: PEPTIDE
<222> LOCATION: (0)...(0)
<223> OTHER INFORMATION: Dfn20 (THG2_WHEAT)

<400> SEQUENCE: 43

Lys Val Cys Arg Gln Arg Ser Ala Gly Phe Lys Gly Pro Cys Val Ser
1               5                   10                  15

Asp Lys Asn Cys Ala Gln Val Cys Leu Gln Glu Gly Trp Gly Gly Gly
            20                  25                  30

Asn Cys Asp Gly Pro Phe Arg Arg Cys Lys Cys Ile Arg Gln Cys
        35                  40                  45

<210> SEQ ID NO 44
<211> LENGTH: 48
<212> TYPE: PRT
<213> ORGANISM: Sorghum bicolor
<220> FEATURE:
<221> NAME/KEY: PEPTIDE
<222> LOCATION: (0)...(0)
<223> OTHER INFORMATION: Dfn21 (SIA2_SORBI)

<400> SEQUENCE: 44

Arg Val Cys Met Gly Lys Ser Ala Gly Phe Lys Gly Leu Cys Met Arg
1               5                   10                  15

Asp Gln Asn Cys Ala Gln Val Cys Leu Gln Glu Gly Trp Gly Gly Gly
            20                  25                  30

Asn Cys Asp Gly Val Met Arg Gln Cys Lys Cys Ile Arg Gln Cys Trp
```

<210> SEQ ID NO 45
<211> LENGTH: 49
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Dfn22 (BAB67948)

<400> SEQUENCE: 45

Ile Ile Cys Lys Ala Arg Ser Lys Met Tyr Arg Gly Lys Cys Arg Gly
1               5                   10                  15

Asn Arg Asn Cys Ala Met Ile Cys Val His Glu Glu Tyr Thr Gly Gly
            20                  25                  30

Tyr Cys Ser Lys Gly Val Phe Ser Lys Cys Met Cys Thr Lys Arg Cys
        35                  40                  45

Gly

<210> SEQ ID NO 46
<211> LENGTH: 51
<212> TYPE: PRT
<213> ORGANISM: Picea abies
<220> FEATURE:
<221> NAME/KEY: PEPTIDE
<222> LOCATION: (0)...(0)
<223> OTHER INFORMATION: Dfn23 (T14866)

<400> SEQUENCE: 46

Gly Arg Thr Cys Lys Thr Pro Ser Gly Lys Phe Lys Gly Val Cys Ala
1               5                   10                  15

Ser Ser Asn Asn Cys Lys Asn Val Cys Gln Thr Glu Gly Phe Pro Ser
            20                  25                  30

Gly Ser Cys Asp Phe His Val Ala Asn Arg Lys Cys Tyr Cys Ser Lys
        35                  40                  45

Pro Cys Pro
50

<210> SEQ ID NO 47
<211> LENGTH: 47
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: Dfn24 (NP_176302)

<400> SEQUENCE: 47

Arg Thr Cys Glu Thr Ser Ser Asn Leu Phe Asn Gly Pro Cys Leu Ser
1               5                   10                  15

Ser Ser Asn Cys Ala Asn Val Cys His Asn Glu Gly Phe Ser Asp Gly
            20                  25                  30

Asp Cys Arg Gly Phe Arg Arg Arg Cys Leu Cys Thr Arg Pro Cys
        35                  40                  45

<210> SEQ ID NO 48
<211> LENGTH: 48
<212> TYPE: PRT
<213> ORGANISM: Capsicum annuum
<220> FEATURE:
<221> NAME/KEY: PEPTIDE
<222> LOCATION: (0)...(0)
<223> OTHER INFORMATION: Dfn27 (CAA65045)

<400> SEQUENCE: 48

Lys Ile Cys Glu Ala Leu Ser Gly Asn Phe Lys Gly Leu Cys Leu Ser
1               5                   10                  15

Ser Arg Asp Cys Gly Asn Val Cys Arg Arg Glu Gly Phe Thr Ser Gly
            20                  25                  30

Val Cys Arg Gly Phe Pro Leu Lys Cys Phe Cys Arg Lys Pro Gly Ala
        35                  40                  45

<210> SEQ ID NO 49
<211> LENGTH: 47
<212> TYPE: PRT
<213> ORGANISM: Phaseolus coccineus
<220> FEATURE:
<221> NAME/KEY: PEPTIDE
<222> LOCATION: (0)...(0)
<223> OTHER INFORMATION: Dfn28 (AF293407_1)

<400> SEQUENCE: 49

Arg Val Cys Glu Ser Gln Ser His Gly Phe Lys Gly Ala Cys Thr Gly
1               5                   10                  15

Asp His Asn Cys Ala Leu Val Cys Arg Asn Glu Gly Phe Ser Gly Gly
            20                  25                  30

Asn Cys Arg Gly Phe Arg Arg Arg Cys Phe Cys Thr Lys Ile Cys
        35                  40                  45

<210> SEQ ID NO 50
<211> LENGTH: 47
<212> TYPE: PRT
<213> ORGANISM: Glycine max
<220> FEATURE:
<221> NAME/KEY: PEPTIDE
<222> LOCATION: (0)...(0)
<223> OTHER INFORMATION: Dfn29 (S51637)

<400> SEQUENCE: 50

Arg Val Cys Glu Ser Gln Ser His Gly Phe His Gly Leu Cys Asn Arg
1               5                   10                  15

Asp His Asn Cys Ala Leu Val Cys Arg Asn Glu Gly Phe Ser Gly Gly
            20                  25                  30

Arg Cys Lys Gly Phe Arg Arg Arg Cys Phe Cys Thr Arg Ile Cys
        35                  40                  45

<210> SEQ ID NO 51
<211> LENGTH: 47
<212> TYPE: PRT
<213> ORGANISM: Castanea sativa
<220> FEATURE:
<221> NAME/KEY: PEPTIDE
<222> LOCATION: (0)...(0)
<223> OTHER INFORMATION: Dfn30 (AF417297_1)

<400> SEQUENCE: 51

Arg Thr Cys Glu Ser Gln Ser His Arg Phe Lys Gly Pro Cys Val Arg
1               5                   10                  15

Lys Ser Asn Cys Ala Ser Val Cys Gln Thr Glu Gly Phe His Gly Gly
            20                  25                  30

Gln Cys Arg Gly Phe Arg Arg Arg Cys Phe Cys Thr Lys His Cys
        35                  40                  45

<210> SEQ ID NO 52
<211> LENGTH: 47
<212> TYPE: PRT

<213> ORGANISM: Arabidopsis thaliana
<220> FEATURE:
<221> NAME/KEY: PEPTIDE
<222> LOCATION: (0)...(0)
<223> OTHER INFORMATION: Dfn31 (NP_201171)

<400> SEQUENCE: 52

Arg Thr Cys Gln Ser Lys Ser His His Phe Lys Tyr Met Cys Thr Ser
1               5                   10                  15

Asn His Asn Cys Ala Ile Val Cys Arg Asn Glu Gly Phe Ser Gly Gly
            20                  25                  30

Arg Cys His Gly Phe His Arg Arg Cys Tyr Cys Thr Arg Leu Cys
        35                  40                  45

<210> SEQ ID NO 53
<211> LENGTH: 47
<212> TYPE: PRT
<213> ORGANISM: Pyrus pyrifolia
<220> FEATURE:
<221> NAME/KEY: PEPTIDE
<222> LOCATION: (0)...(0)
<223> OTHER INFORMATION: Dfn32 (BAB64929)

<400> SEQUENCE: 53

Arg Thr Cys Glu Ala Ala Ser Gly Lys Phe Lys Gly Met Cys Phe Ser
1               5                   10                  15

Ser Asn Asn Cys Ala Asn Thr Cys Ala Arg Glu Lys Phe Asp Gly Gly
            20                  25                  30

Lys Cys Lys Gly Phe Arg Arg Arg Cys Met Cys Thr Lys Lys Cys
        35                  40                  45

<210> SEQ ID NO 54
<211> LENGTH: 48
<212> TYPE: PRT
<213> ORGANISM: Capsicum annuum
<220> FEATURE:
<221> NAME/KEY: PEPTIDE
<222> LOCATION: (0)...(0)
<223> OTHER INFORMATION: Dfn33 (DEF1_CAPAN)

<400> SEQUENCE: 54

Lys Ile Cys Glu Ala Leu Ser Gly Asn Phe Lys Gly Leu Cys Leu Ser
1               5                   10                  15

Ser Arg Asp Cys Gly Asn Val Cys Arg Arg Glu Gly Phe Thr Asp Gly
            20                  25                  30

Ser Cys Ile Gly Phe Arg Leu Gln Cys Phe Cys Thr Lys Pro Cys Ala
        35                  40                  45

<210> SEQ ID NO 55
<211> LENGTH: 48
<212> TYPE: PRT
<213> ORGANISM: Oryza sativa
<220> FEATURE:
<221> NAME/KEY: PEPTIDE
<222> LOCATION: (0)...(0)
<223> OTHER INFORMATION: Dfn34 (T02667)

<400> SEQUENCE: 55

Arg Thr Cys Glu Ser Gln Ser His Arg Phe Lys Gly Pro Cys Ala Arg
1               5                   10                  15

Lys Ala Asn Cys Ala Ser Val Cys Asn Thr Glu Gly Phe Pro Asp Gly
            20                  25                  30

Tyr Cys His Gly Val Arg Arg Arg Cys Met Cys Thr Lys Pro Cys Pro
        35                  40                  45

<210> SEQ ID NO 56
<211> LENGTH: 47
<212> TYPE: PRT
<213> ORGANISM: Petunia integrifolia
<220> FEATURE:
<221> NAME/KEY: PEPTIDE
<222> LOCATION: (0)...(0)
<223> OTHER INFORMATION: Dfn35 (THG_PETIN)

<400> SEQUENCE: 56

Arg Thr Cys Glu Ser Gln Ser His Arg Phe His Gly Thr Cys Val Arg
1               5                   10                  15

Glu Ser Asn Cys Ala Ser Val Cys Gln Thr Glu Gly Phe Ile Gly Gly
            20                  25                  30

Asn Cys Arg Ala Phe Arg Arg Arg Cys Phe Cys Thr Arg Asn Cys
        35                  40                  45

<210> SEQ ID NO 57
<211> LENGTH: 48
<212> TYPE: PRT
<213> ORGANISM: Nicotiana tabacum
<220> FEATURE:
<221> NAME/KEY: PEPTIDE
<222> LOCATION: (0)...(0)
<223> OTHER INFORMATION: Dfn36 (THGF_TOBAC)

<400> SEQUENCE: 57

Arg Glu Cys Lys Thr Glu Ser Asn Thr Phe Pro Gly Ile Cys Ile Thr
1               5                   10                  15

Lys Pro Pro Cys Arg Lys Ala Cys Ile Ser Glu Lys Phe Thr Asp Gly
            20                  25                  30

His Cys Ser Lys Leu Leu Arg Arg Cys Leu Cys Thr Lys Pro Cys Val
        35                  40                  45

<210> SEQ ID NO 58
<211> LENGTH: 58
<212> TYPE: PRT
<213> ORGANISM: Helianthus annuus
<220> FEATURE:
<221> NAME/KEY: PEPTIDE
<222> LOCATION: (0)...(0)
<223> OTHER INFORMATION: Dfn38 (THGF_HELAN)

<400> SEQUENCE: 58

Asn Glu Met Gly Gly Pro Leu Val Val Glu Ala Arg Thr Cys Glu Ser
1               5                   10                  15

Gln Ser His Lys Phe Lys Gly Thr Cys Leu Ser Asp Thr Asn Cys Ala
            20                  25                  30

Asn Val Cys His Ser Glu Arg Phe Ser Gly Gly Lys Cys Arg Gly Phe
        35                  40                  45

Arg Arg Arg Cys Phe Cys Thr Thr His Cys
    50                  55

<210> SEQ ID NO 59
<211> LENGTH: 47
<212> TYPE: PRT
<213> ORGANISM: Brassica rapa
<220> FEATURE:
<221> NAME/KEY: PEPTIDE
<222> LOCATION: (0)...(0)
<223> OTHER INFORMATION: Dfn39 (T14395)

<400> SEQUENCE: 59

```
Arg Thr Cys Glu Ser Lys Ser His Arg Phe Lys Gly Thr Cys Val Ser
1               5                   10                  15

Ser Thr Asn Cys Gly Asn Val Cys His Asn Glu Gly Phe Gly Gly Gly
        20                  25                  30

Lys Cys Arg Gly Phe Arg Val Arg Cys Tyr Cys Thr Arg His Cys
35                  40                  45
```

<210> SEQ ID NO 60
<211> LENGTH: 55
<212> TYPE: PRT
<213> ORGANISM: Solanum tuberosum
<220> FEATURE:
<221> NAME/KEY: PEPTIDE
<222> LOCATION: (0)...(0)
<223> OTHER INFORMATION: Dfn40 (P322_SOLTU)

<400> SEQUENCE: 60

```
Gly Pro Met Arg Ile Ala Glu Ala Arg His Cys Glu Ser Leu Ser His
1               5                   10                  15

Arg Phe Lys Gly Pro Cys Thr Arg Asp Ser Asn Cys Ala Ser Val Cys
        20                  25                  30

Glu Thr Glu Arg Phe Ser Gly Gly Asn Cys His Gly Phe Arg Arg Arg
35                  40                  45

Cys Phe Cys Thr Lys Pro Cys
50                  55
```

<210> SEQ ID NO 61
<211> LENGTH: 47
<212> TYPE: PRT
<213> ORGANISM: Capsicum annuum
<220> FEATURE:
<221> NAME/KEY: PEPTIDE
<222> LOCATION: (0)...(0)
<223> OTHER INFORMATION: Dfn41 (DEF2_CAPAN)

<400> SEQUENCE: 61

```
Arg Thr Cys Glu Ser Gln Ser His Arg Phe Lys Gly Leu Cys Phe Ser
1               5                   10                  15

Lys Ser Asn Cys Gly Ser Val Cys His Thr Glu Gly Phe Asn Gly Gly
        20                  25                  30

His Cys Arg Gly Phe Arg Arg Arg Cys Phe Cys Thr Arg His Cys
35                  40                  45
```

<210> SEQ ID NO 62
<211> LENGTH: 47
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: Dfn42 (NP_178320)

<400> SEQUENCE: 62

```
Arg Thr Cys Ala Ser Gln Ser Gln Arg Phe Lys Gly Lys Cys Val Ser
1               5                   10                  15

Asp Thr Asn Cys Glu Asn Val Cys His Asn Glu Gly Phe Pro Gly Gly
        20                  25                  30

Asp Cys Arg Gly Phe Arg Arg Arg Cys Phe Cys Thr Arg Asn Cys
35                  40                  45
```

<210> SEQ ID NO 63
<211> LENGTH: 47
<212> TYPE: PRT

<213> ORGANISM: Arabidopsis thaliana
<220> FEATURE:
<221> NAME/KEY: PEPTIDE
<222> LOCATION: (0)...(0)
<223> OTHER INFORMATION: Dfn43 (NP_178319)

<400> SEQUENCE: 63

Arg Thr Cys Glu Ser Gln Ser His Arg Phe Lys Gly Thr Cys Val Ser
1               5                   10                  15

Ala Ser Asn Cys Ala Asn Val Cys His Asn Glu Gly Phe Val Gly Gly
            20                  25                  30

Asn Cys Arg Gly Phe Arg Arg Arg Cys Phe Cys Thr Arg His Cys
        35                  40                  45

<210> SEQ ID NO 64
<211> LENGTH: 56
<212> TYPE: PRT
<213> ORGANISM: Lycopersicon lycopersicon
<220> FEATURE:
<221> NAME/KEY: PEPTIDE
<222> LOCATION: (0)...(0)
<223> OTHER INFORMATION: Dfn44 (CAB42006)

<400> SEQUENCE: 64

Thr Gly Pro Met Arg Ile Val Glu Ala Arg Thr Cys Glu Ser Gln Ser
1               5                   10                  15

His Arg Phe Lys Gly Pro Cys Val Ser Glu Lys Asn Cys Ala Ser Val
            20                  25                  30

Cys Glu Thr Glu Gly Phe Ser Gly Gly Asp Cys Arg Gly Phe Arg Arg
        35                  40                  45

Arg Cys Phe Cys Thr Arg Pro Cys
50                  55

<210> SEQ ID NO 65
<211> LENGTH: 47
<212> TYPE: PRT
<213> ORGANISM: Glycine max
<220> FEATURE:
<221> NAME/KEY: PEPTIDE
<222> LOCATION: (0)...(0)
<223> OTHER INFORMATION: Dfn45 (T06381)

<400> SEQUENCE: 65

Arg Thr Cys Glu Ser Gln Ser His Arg Phe Lys Gly Pro Cys Leu Ser
1               5                   10                  15

Asp Thr Asn Cys Gly Ser Val Cys Arg Thr Glu Arg Phe Thr Gly Gly
            20                  25                  30

His Cys Arg Gly Phe Arg Arg Arg Cys Phe Cys Thr Lys His Cys
        35                  40                  45

<210> SEQ ID NO 66
<211> LENGTH: 57
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: Dfn46 (NP_178321)

<400> SEQUENCE: 66

Thr Gly Met Gly Pro Val Thr Val Glu Ala Arg Thr Cys Glu Ser Lys
1               5                   10                  15

Ser His Arg Phe Lys Gly Pro Cys Val Ser Thr His Asn Cys Ala Asn
            20                  25                  30

Val Cys His Asn Glu Gly Phe Gly Gly Gly Lys Cys Arg Gly Phe Arg
35                  40                  45

Arg Arg Cys Tyr Cys Thr Arg His Cys
50                  55

<210> SEQ ID NO 67
<211> LENGTH: 58
<212> TYPE: PRT
<213> ORGANISM: Capsicum annuum
<220> FEATURE:
<221> NAME/KEY: PEPTIDE
<222> LOCATION: (0)...(0)
<223> OTHER INFORMATION: Dfn47 (AF442388_1)

<400> SEQUENCE: 67

Thr Glu Met Gly Pro Met Arg Ile Val Glu Ala Arg Thr Cys Glu Ser
1               5                   10                  15

Gln Ser His Arg Phe Lys Gly Val Cys Ala Ser Glu Thr Asn Cys Ala
            20                  25                  30

Ser Val Cys Gln Thr Glu Gly Phe Ser Gly Gly Asp Cys Arg Gly Phe
35                  40                  45

Arg Arg Arg Cys Phe Cys Thr Arg Pro Cys
50                  55

<210> SEQ ID NO 68
<211> LENGTH: 58
<212> TYPE: PRT
<213> ORGANISM: Nicotiana tabacum
<220> FEATURE:
<221> NAME/KEY: PEPTIDE
<222> LOCATION: (0)...(0)
<223> OTHER INFORMATION: Dfn48 (BAA95697)

<400> SEQUENCE: 68

Thr Glu Met Gly Pro Met Thr Ile Ala Glu Ala Arg Thr Cys Glu Ser
1               5                   10                  15

Gln Ser His Arg Phe Lys Gly Pro Cys Ser Arg Asp Ser Asn Cys Ala
            20                  25                  30

Thr Val Cys Leu Thr Glu Gly Phe Ser Gly Gly Asp Cys Arg Gly Phe
35                  40                  45

Arg Arg Arg Cys Phe Cys Thr Arg Pro Cys
50                  55

<210> SEQ ID NO 69
<211> LENGTH: 46
<212> TYPE: PRT
<213> ORGANISM: Lycopersicon lycopersicon
<220> FEATURE:
<221> NAME/KEY: PEPTIDE
<222> LOCATION: (0)...(0)
<223> OTHER INFORMATION: Dfn51 (12635700_EST)

<400> SEQUENCE: 69

Ile Cys Glu Ser Leu Ser His Arg Phe Lys Gly Pro Cys Val Ser Asp
1               5                   10                  15

Lys Asn Cys Ala Ser Val Cys Glu Thr Glu Arg Phe Ser Gly Gly Asn
            20                  25                  30

Cys Arg Gly Phe Arg Arg Arg Cys Phe Cys Thr Lys Pro Cys
35                  40                  45

<210> SEQ ID NO 70
<211> LENGTH: 47

```
<212> TYPE: PRT
<213> ORGANISM: Lycopersicon lycopersicon
<220> FEATURE:
<221> NAME/KEY: PEPTIDE
<222> LOCATION: (0)...(0)
<223> OTHER INFORMATION: Dfn52 (13680747_EST)

<400> SEQUENCE: 70

Ile Cys Glu Ala Pro Ser Gln Thr Phe Pro Gly Leu Cys Phe Met Asp
1               5                   10                  15

Ser Ser Cys Arg Arg Tyr Cys Ile Lys Glu Arg Phe Thr Gly Gly His
            20                  25                  30

Cys Ser Lys Leu Gln Arg Lys Cys Leu Cys Thr Lys Pro Cys Val
        35                  40                  45

<210> SEQ ID NO 71
<211> LENGTH: 47
<212> TYPE: PRT
<213> ORGANISM: Lycopersicon lycopersicon
<220> FEATURE:
<221> NAME/KEY: PEPTIDE
<222> LOCATION: (0)...(0)
<223> OTHER INFORMATION: Dfn53 (16240393_EST)

<400> SEQUENCE: 71

Met Cys Glu Ser Thr Ser Gln Thr Phe Lys Gly Leu Cys Phe Thr Asp
1               5                   10                  15

Ser Ser Cys Arg Lys Ala Cys Val Thr Glu Glu Phe Thr Gly Gly His
            20                  25                  30

Cys Ser Lys Leu Gln Arg Lys Cys Leu Cys Thr Lys Val Cys Val
        35                  40                  45

<210> SEQ ID NO 72
<211> LENGTH: 47
<212> TYPE: PRT
<213> ORGANISM: Lycopersicon pennellii
<220> FEATURE:
<221> NAME/KEY: PEPTIDE
<222> LOCATION: (0)...(0)
<223> OTHER INFORMATION: Dfn54 (6918121_EST)

<400> SEQUENCE: 72

Arg Thr Cys Lys Ala Pro Ser Gln Thr Phe Pro Gly Leu Cys Phe Met
1               5                   10                  15

Asp Ser Ser Cys Arg Lys Tyr Cys Ile Lys Glu Lys Phe Thr Gly Gly
            20                  25                  30

His Cys Ser Thr Leu Gln Arg Arg Cys Leu Cys Thr Lys Pro Cys
        35                  40                  45

<210> SEQ ID NO 73
<211> LENGTH: 47
<212> TYPE: PRT
<213> ORGANISM: Lycopersicon lycopersicon
<220> FEATURE:
<221> NAME/KEY: PEPTIDE
<222> LOCATION: (0)...(0)
<223> OTHER INFORMATION: Dfn55 (14084224_EST)

<400> SEQUENCE: 73

Arg Thr Cys Glu Ser Gln Ser Asn Ser Phe Lys Gly Thr Cys Val Arg
1               5                   10                  15

Asp Ser Asn Cys Ala Thr Val Cys Gln Thr Glu Gly Phe Ile Gly Gly
            20                  25                  30

Asn Cys Arg Gly Phe Arg Arg Arg Cys Phe Cys Thr Arg Asn Cys
```

<210> SEQ ID NO 74
<211> LENGTH: 47
<212> TYPE: PRT
<213> ORGANISM: Solanum tuberosum
<220> FEATURE:
<221> NAME/KEY: PEPTIDE
<222> LOCATION: (0)...(0)
<223> OTHER INFORMATION: Dfn57 (17072269_EST)

<400> SEQUENCE: 74

```
Arg Thr Cys Glu Ser Gln Ser His Lys Tyr Lys Gly Pro Cys Val Arg
1               5                   10                  15

Lys Ser Asn Cys Gly Ala Val Cys Gln Thr Glu Gly Phe Thr Gly Gly
            20                  25                  30

His Cys Arg Gly Val Arg Arg Cys Phe Cys Thr Lys His Cys
        35                  40                  45
```

<210> SEQ ID NO 75
<211> LENGTH: 47
<212> TYPE: PRT
<213> ORGANISM: Solanum tuberosum
<220> FEATURE:
<221> NAME/KEY: PEPTIDE
<222> LOCATION: (0)...(0)
<223> OTHER INFORMATION: Dfn58 (20165169_EST)

<400> SEQUENCE: 75

```
Arg His Cys Glu Ser Leu Ser His Arg Phe Lys Gly Pro Cys Ala Ser
1               5                   10                  15

Asp Arg Asn Cys Ala Ser Val Cys Glu Thr Glu Arg Phe Ser Gly Gly
            20                  25                  30

Asn Cys Arg Gly Phe Arg Arg Leu Cys Phe Cys Thr Lys Pro Cys
        35                  40                  45
```

<210> SEQ ID NO 76
<211> LENGTH: 58
<212> TYPE: PRT
<213> ORGANISM: Lycopersicon lycopersicon
<220> FEATURE:
<221> NAME/KEY: PEPTIDE
<222> LOCATION: (0)...(0)
<223> OTHER INFORMATION: Dfn59 (7409753_EST)

<400> SEQUENCE: 76

```
Thr Glu Met Gly Pro Thr Arg Ile Val Glu Ala Arg His Cys Glu Ser
1               5                   10                  15

Leu Ser His Arg Phe Lys Gly Pro Cys Val Ser Asp Lys Asn Cys Ala
            20                  25                  30

Ser Val Cys Glu Thr Glu Arg Phe Ser Gly Gly Asn Cys Arg Gly Phe
        35                  40                  45

Arg Arg Arg Cys Phe Cys Thr Arg Pro Cys
50                  55
```

<210> SEQ ID NO 77
<211> LENGTH: 58
<212> TYPE: PRT
<213> ORGANISM: Solanum tuberosum
<220> FEATURE:
<221> NAME/KEY: PEPTIDE
<222> LOCATION: (0)...(0)
<223> OTHER INFORMATION: Dfn60 (15256358_EST)

<400> SEQUENCE: 77

-continued

```
Thr Glu Met Gly Pro Met Arg Ile Val Glu Ala Arg His Cys Glu Ser
1               5                   10                  15

Leu Ser His Arg Phe Lys Gly Pro Cys Ala Ser Asp Lys Asn Cys Ala
20                  25                  30

Ser Val Cys Glu Thr Glu Arg Phe Ser Gly Gly Asn Cys Arg Gly Phe
35                  40                  45

Arg Arg Arg Cys Phe Cys Thr Arg Pro Cys
50                  55

<210> SEQ ID NO 78
<211> LENGTH: 58
<212> TYPE: PRT
<213> ORGANISM: Lycopersicon lycopersicon
<220> FEATURE:
<221> NAME/KEY: PEPTIDE
<222> LOCATION: (0)...(0)
<223> OTHER INFORMATION: Dfn61 (16240055_EST)

<400> SEQUENCE: 78

Thr Glu Met Gly Pro Met Arg Ile Val Glu Ala Arg Thr Cys Glu Ser
1               5                   10                  15

Gln Ser His Arg Pro Lys Val Val Cys Lys Ser Glu Thr Asn Cys Ala
20                  25                  30

Glu Val Cys Gln Thr Glu Gly Phe Ser Gly Gly Asp Cys Arg Gly Phe
35                  40                  45

Arg Arg Arg Cys Phe Cys Thr Arg Pro Cys
50                  55
```

METHODS OF PROTECTING PLANTS FROM PATHOGENIC FUNGI

CROSS REFERENCE TO RELATED APPLICATIONS

This application is a divisional of U.S. Ser. No. 11/172,571, now U.S. Pat. No. 7,332,650, filed on Jun. 30, 2005, which claims the benefit of U.S. Provisional Application No. 60/584,905, filed on Jun. 30, 2004, both of which are herein incorporated by reference in their entirety.

FIELD OF THE INVENTION

The present invention relates to methods of protecting plants from fungal pathogens through the use of polypeptides having antifungal activity and the nucleic acid sequences that encode them. Methods of the invention utilize these polypeptides and nucleic acid sequences to control plant fungal pathogens and to increase fungal pathogen resistance in plants. Transgenic plants and seeds are also included.

BACKGROUND OF THE INVENTION

Disease in plants results from biotic and abiotic causes. A host of cellular processes enables plants to defend themselves from disease caused by pathogenic agents. These processes apparently form an integrated set of resistance mechanisms that is activated by initial infection and then limits further spread of the invading pathogenic organism.

Subsequent to recognition of a plant pathogen, plants can activate an array of biochemical responses. Generally, the plant responds by inducing several local responses in the cells immediately surrounding the infection site. The most common resistance response observed in both nonhost and race-specific interactions is termed the "hypersensitive response" (HR). In the hypersensitive response, cells contacted by the pathogen, and often neighboring cells, rapidly collapse and dry in a necrotic fleck. Other responses include the deposition of callose, the physical thickening of cell walls by lignification, and the synthesis of various antibiotic small molecules and proteins. Genetic factors in both the host and the pathogen determine the specificity of these local responses, which can be very effective in limiting the spread of infection.

Incidence of plant diseases has traditionally been controlled by agronomic practices that include crop rotation, the use of agrochemicals, and conventional breeding techniques. The use of chemicals to control plant pathogens, however, increases costs to farmers and causes harmful effects on the ecosystem. Consumers and government regulators alike are becoming increasingly concerned with the environmental hazards associated with the production and use of synthetic agrochemicals for protecting plants from pathogens. Because of such concerns, regulators have banned or limited the use of some of the most hazardous chemicals. The incidence of fungal diseases has been controlled to some extent by breeding resistant crops. Traditional breeding methods, however, are time-consuming and require continuous effort to maintain disease resistance as pathogens evolve. See, for example, Grover and Gowthaman (2003) Curr. Sci. 84:330-340. Thus, there is a significant need for novel alternatives for the control of plant pathogens that possess a lower risk of pollution and environmental hazards than is characteristic of traditional agrochemical-based methods and that are less cumbersome than conventional breeding techniques.

Recently, agricultural scientists have developed crop plants with enhanced pathogen resistance by genetically engineering plants to express antipathogenic proteins. For example, potatoes and tobacco plants genetically engineered to produce an antifungal endochitinase protein were shown to exhibit increased resistance to foliar and soil-borne fungal pathogens. See Lorito et al. (1998) Proc. Natl. Acad. Sci. 95:7860-7865. Moreover, transgenic barley that is resistant to the stem rust fungus has also been developed. See Horvath et al. (2003) Proc. Natl. Acad. Sci. 100:364-369. A continuing effort to identify antipathogenic agents and to genetically engineer disease-resistant plants is underway.

Various approaches to pathogen control have been tried including the use of biological organisms which are typically "natural predators" of the species sought to be controlled. Such predators may include other insects, fungi, and bacteria such as Bacillus thuringiensis. Alternatively, large colonies of insect pests have been raised in captivity, sterilized and released into the environment in the hope that mating between the sterilized insects and fecund wild insects will decrease the insect population. While these approaches have had some success, they entail considerable expense and present several major difficulties. For example, it is difficult both to apply biological organisms to large areas and to cause such living organisms to remain in the treated area or on the treated plant species for an extended time. Predator insects can migrate and fungi or bacteria can be washed off of a plant or removed from a treated area by rain. Consequently, while the use of such biological controls has desirable characteristics and has met with some success, in practice these methods have not achieved the goal of controlling pathogen damage to crops.

Advances in biotechnology have presented new opportunities for pathogen control through genetic engineering. In particular, advances in plant genetics coupled with the identification of naturally-occurring plant defensive compounds or agents offer the opportunity to create transgenic crop plants capable of producing such defensive agents and thereby protect the plants against disease.

Thus, in light of the significant impact of plant fungal pathogens on the yield and quality of crops, new methods for protecting plants from such pathogens are needed.

BRIEF SUMMARY OF THE INVENTION

The embodiments of the invention provide transgenic plants with enhanced resistance to fungal pathogens, each plant comprising a polynucleotide encoding a polypeptide comprising an amino acid sequence at least 95% identical to SEQ ID NOs: 1, 2, 4, 5, 7, 8, 10, 11, 13, 14, 16, 17, 19, 20, 22, 23, 25, 26, 28 or 29 wherein said plant has improved resistance to at least one plant pathogenic fungus. The plant may be a monocot or a dicot. Seeds of such transgenic plants are also provided for. Similarly, the embodiments provide monocot or dicot transgenic plants and seeds with enhanced resistance to fungal pathogens wherein the plant comprises a polynucleotide sequence at least 95% identical to SEQ ID NOs: 3, 6, 9, 12, 15, 18, 21, 24, 27 or 30 wherein said plant has improved pathogen resistance to at least one plant pathogenic fungus. The polypeptides expressed in the transgenic plants may or may not comprise a signal sequence.

The embodiments of the invention also provide methods of enhancing resistance of a plant to a fungal pathogen, the methods comprising introducing into a plant cell an expression cassette comprising a nucleotide sequence operably linked to a promoter, wherein the nucleotide sequence has at least 95% identity to SEQ ID NOs: 3, 6, 9, 12, 15, 18, 21, 24, 27 or 30 or wherein the nucleotide sequence encodes a polypeptide comprising an amino acid sequence identical or substantially identical to SEQ ID NOs: 1, 2, 4, 5, 7, 8, 10, 11, 13, 14, 16, 17, 19, 20, 22, 23, 25, 26, 28 or 29, and wherein the polypeptide has activity against at least one plant pathogenic fungus. The plant cell is used to regenerate a transformed plant wherein the level of fungal pathogen resistance in the transformed plant is increased in comparison to a plant that does not comprise the expression cassette. The polypeptides of these embodiments may or may not comprise a signal sequence.

The promoters used in the expression cassettes of the embodiments are selected from the group consisting of constitutive, tissue-specific, root-specific, inducible and pathogen-inducible promoters. In some embodiments, the polypeptide with activity against plant fungal pathogens comprises a signal sequence. In some embodiments, the polypeptide lacks a signal sequence. In some embodiments, the signal sequence is a secretion signal sequence, while in others it is an organelle and/or plastid signal sequence.

DETAILED DESCRIPTION OF THE INVENTION

Embodiments of the invention provide compositions and methods directed to enhancing plant fungal pathogen resistance. The embodiments provide polynucleotides encoding amino acid sequences for antifungal polypeptides. Specifically, the embodiments provide antifungal polypeptides having the amino acid sequences set forth in SEQ ID NOs: 1, 2, 4, 5, 7, 8, 10 and 11 and variants and fragments thereof. Isolated nucleic acid molecules, and variants and fragments thereof, comprising nucleotide sequences that encode the amino acid sequences shown in SEQ ID NOs: 1, 2, 4, 5, 7, 8, 10 and 11 are further provided.

Nucleotide sequences that encode the polypeptides of SEQ ID NOs: 1, 2, 4, 5, 7, 8, 10 and 11 are provided. These nucleotide sequences are set forth in SEQ ID NOs:3, 6, 9, 12, 13, and 14. Some of these nucleotide sequences have been optimized for expression in *E. coli*. Plants, plant cells, seeds, and microorganisms comprising a nucleotide sequence that encodes an antifungal polypeptide of the embodiments are also disclosed herein. Antifungal compositions comprising an isolated antifungal polypeptide or a microorganism that expresses a polypeptide of the embodiments are further provided. The compositions of the embodiments find use in generating fungal-resistant plants and in protecting plants from plant pathogenic fungi.

The polypeptides disclosed herein also display antifungal activity against plant pathogenic fungi, such as, for example, *Alternaria brassicicola, Fusarium verticillioides, Botrytis cinerea, Fusarium oxysporum* and *Verticillium dahliae*. The species of origin of these antifungal polypeptides are plant species. In particular, the source of the polypeptides of SEQ ID NOs: 1 and 2 is *Brassica napus*. The source of the polypeptides of SEQ ID NOs: 4 and 5 is *Arabidopsis thaliana*. The source of the polypeptides of SEQ ID NOs: 7 and 8 is *Vigna radiata*. The source of the polypeptides of SEQ ID NOs: 10 and 11 is *Vicia faba*. The source of the polypeptides of SEQ ID NOs: 13 and 14 is *Nicotiana excelsior*. The source of the polypeptides of SEQ ID NOs: 16 and 17 is *Musa acuminata*. The source of the polypeptides of SEQ ID NOs: 19 and 20 is *Glycine max*. The source of the polypeptides of SEQ ID NOs: 22 and 23 is *Citrus x paradisi*. The source of the polypeptides of SEQ ID NOs: 25 and 26 is *Nicotiana paniculata*. The source of the polypeptides of SEQ ID NOs: 28 and 29 is *Lycopersicon lycopersicon*.

"Antifungal compositions" or "antifungal polypeptides" is intended to mean that the compositions or polypeptides of the embodiments have antifungal activity and thus are capable of suppressing, controlling, and/or killing the invading fungus.

An antifungal polypeptide of the embodiments will reduce the disease symptoms resulting from fungal challenge by at least about 5% to about 50%, at least about 10% to about 60%, at least about 30% to about 70%, at least about 40% to about 80%, or at least about 50% to about 90% or greater. Hence, the methods of the embodiments can be utilized to protect plants from pathogenic fungi.

The polynucleotides and polypeptides of the embodiments find use in methods for inducing fungal pathogen resistance in a plant. Accordingly, the compositions and methods disclosed herein are useful in protecting plants against pathogenic fungi. "Fungal pathogen resistance" is intended to mean that the plant avoids the disease symptoms that are the outcome of plant-fungus interactions. A plant with "improved fungal pathogen resistance" or "enhanced fungal pathogen resistance" is intended to mean that a plant, which has been transformed with a nucleic acid molecule of the embodiments, and which is expressing a polypeptide of the embodiments, exhibits a level of resistance or tolerance to a fungal pathogen that is increased in comparison to a plant that does not comprise said nucleic acid molecule, such as a wild type plant. That is, fungi are prevented from causing plant disease and the associated disease symptoms in the transformed plant, or alternatively, the disease symptoms caused by the fungus are minimized or lessened, such as, for example, the reduction of stress and associated yield loss. Resistance may vary from a slight increase in tolerance to the effects of the fungal pathogen to total resistance such that the plant is unaffected by the presence of the fungal pathogen. An increased level of resistance against a particular fungus or against a wider spectrum of fungi may both constitute antifungal activity and improved fungus resistance. The plants of the embodiments exhibit an improvement of at least 5%, at least 10%, at least 20%, at least 30%, at least 40%, at least 50%, at least 55%, at least 60%, at least 65%, at least 70%, at least 75%, at least 80%, at least 85%, at least 90%, at least 95%, or up to 100% improvement compared to an untransformed plant. Such improvement may be measured by any suitable means known in the art, such as, but not limited to, counting fungal lesions on plants, measuring fungal biomass, comparing plant yields, and other methods described in the following paragraphs.

Assays that measure antifungal activity are commonly known in the art, as are methods to quantitate disease resistance in plants following fungal pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antifungal polypeptide or having an antifungal composition applied to its surface shows a decrease in tissue necrosis (i.e., lesion diameter) or a decrease in plant death following fungal pathogen challenge when compared to a control plant that was not exposed to the antifungal composition. Alternatively, antifungal activity can be measured by a decrease in fungal biomass. For example, a plant expressing an antifungal polypeptide or exposed to an antifungal composition is challenged with a fungal pathogen of interest. Over time, tissue samples from the fungal pathogen-inoculated tissues are obtained and RNA is extracted. The percent of a specific fungal pathogen RNA transcript relative to the level of a plant specific transcript allows the level of fungal biomass to be determined. See, for example, Thomma et al. (1998) *Plant Biology* 95:15107-15111, herein incorporated by reference.

Furthermore, in vitro antifungal assays include, for example, the addition of varying concentrations of the antifungal composition to paper disks and placing the disks on agar containing a suspension of the fungal pathogen of interest. Following incubation, clear inhibition zones develop around the discs that contain an effective concentration of the antifungal polypeptide (Liu et al. (1994) *Plant Biology* 91:1888-1892, herein incorporated by reference). Additionally, microspectrophotometrical analysis can be used to measure the in vitro antifungal properties of a composition (Hu et al. (1997) *Plant Mol. Biol.* 34:949-959 and Cammue et al. (1992) *J. Biol. Chem.* 267: 2228-2233, both of which are herein incorporated by reference). Assays that specifically measure antifungal activity are also well known in the art. See, for example, Duvick et al. (1992) *J. Biol. Chem.* 267: 18814-18820; Lacadena et al. (1995) *Arch. Biochem. Biophys.* 324:273-281; Xu et al. (1997) *Plant Mol. Biol.* 34: 949-959; Lee et al. (1999) *Biochem. Biophys. Res. Comm.* 263:646-651; Vila et al. (2001) *Mol. Plant. Microbe Interact.* 14:1327-1331; Moreno et al. (2003) *Phytpathol.* 93:1344-1353; Kaiserer et al. (2003) *Arch. Microbiol.* 180:204-210; and U.S. Pat. No. 6,015,941.

The embodiments disclose plants transformed with nucleic acid molecules that encode antifungal proteins. The compositions find use in methods for inducing fungal pathogen resistance in a plant and for protecting a plant from a fungus. One of skill in the art will appreciate that the compositions and methods disclosed herein can be used in combination with other compositions and methods available in the art for protecting plants from fungal pathogen attack.

In particular aspects, methods for inducing fungal resistance in a plant comprise introducing into a plant at least one expression cassette, wherein the expression cassette comprises a nucleotide sequence encoding an antifungal polypeptide of the embodiments operably linked to a promoter that drives expression in the plant. The plant expresses the polypeptide, thereby exposing the fungus to the polypeptide at the site of attack. Expression of a polypeptide of the embodiments may be targeted to specific plant tissues where fungal resistance is particularly important, such as, for example, roots, leaves, or stems. Such tissue-preferred expression may be accomplished by root-preferred, leaf-preferred, vascular tissue-preferred, stalk-preferred, or seed-preferred promoters. Moreover, the polypeptides of the embodiments may also be targeted to specific subcellular locations within a plant cell or, alternatively, secreted from the cell, as described herein below.

Just as expression of a polypeptide of the embodiments may be targeted to specific plant tissues or cell types through the use of appropriate promoters, it may also be targeted to different locations within the cell through the use of targeting information or "targeting labels." Unlike the promoter, which acts at the transcriptional level, such targeting information is part of the initial translation product. Depending on the mode of infection of the fungal pathogen or the metabolic function of the tissue or cell type, the location of the protein in different compartments of the cell may make it more efficacious against a given pathogen or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene.

There are many signal peptides described in the literature, and they are largely interchangeable (Raikhel and Chrispeels, "Protein sorting and vesicle traffic" in Buchanan et al., eds, (2000) *Biochemistry and Molecular Biology of Plants* (American Society of Plant Physiologists, Rockville, Md.), herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the fungal pathogen and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move. This will often be a suitable location.

Other fungal pathogens may be more effectively combated by locating the peptide within the cell rather than outside the cell membrane. This can be accomplished, for example, by adding an endoplasmic reticulum retention signal encoding sequence to the sequence of the gene. Methods and sequences for doing this are described in Raikhel and Chrispeels, supra; for example, adding sequences encoding the amino acids K, D, E and L in that order, or variations thereof described in the literature, to the end of the protein coding portion of the polypeptide will accomplish this. ER retention sequences are well known in the art. See, for example, Denecke et al. (1992). *EMBO J.* 11:2345-2355; Wandelt et al. (1992) *Plant J.* 2:181-192; Denecke et al. (1993) *J. Exp. Bot.* 44:213-221; Vitale et al. (1993) *J. Exp. Bot.* 44:1417-1444; Gomord et al. (1996) *Plant Physiol. Biochem.* 34:165-181; Lehmann et al. (2001) *Plant Physiol.* 127 (2): 436-449.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the embodiments can be produced either from a nucleic acid molecule disclosed herein, or by the use of standard molecular biology techniques. For example, a truncated protein of the embodiments can be produced by expression of a recombinant nucleic acid molecule of the embodiments in an appropriate host cell, or alternatively by a combination of ex vivo procedures, such as protease digestion and purification.

As used herein, the terms "encoding" or "encoded" when used in the context of a specified nucleic acid molecule mean that the nucleic acid molecule comprises the requisite information to direct translation of the nucleotide sequence into a specified protein. The information by which a protein is encoded is specified by the use of codons. A nucleic acid molecule encoding a protein may comprise non-translated sequences (e.g., introns) within translated regions of the nucleic acid sequence or may lack such intervening non-translated sequences (e.g., as in cDNA).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

The embodiments encompass methods of using isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the embodiments or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the embodiments. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have antifungal activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the polypeptides of the embodiments.

A fragment of a nucleotide sequence that encodes a biologically active portion of an antifungal polypeptide of the embodiments will encode at least 15, 25, 30, 40, 50, 60, or 70 contiguous amino acids, or up to the total number of amino acids present in a full-length antifungal polypeptide of the embodiments (for example, 80 amino acids for SEQ ID NO:1). Fragments of a nucleotide sequence that are useful as hybridization probes or PCR primers generally need not encode a biologically active portion of an antifungal protein.

As used herein, "full-length sequence" in reference to a specified polynucleotide means having the entire nucleic acid sequence of a native sequence. "Native sequence" is intended to mean an endogenous sequence, i.e., a non-engineered sequence found in an organism's genome.

Thus, a fragment of a nucleotide sequence of the embodiments may encode a biologically active portion of an antifungal polypeptide, or it may be a fragment that can be used as a hybridization probe or PCR primer using methods disclosed below. A biologically active portion of an antifungal polypeptide can be prepared by isolating a portion of one of the nucleotide sequences of the embodiments, expressing the encoded portion of the antifungal protein (e.g., by recombinant expression in vitro), and assessing the activity of the encoded portion of the antifungal protein. Nucleic acid molecules that are fragments of a nucleotide sequence of the embodiments comprise at least 15, 20, 50, 75, 100, or 150 contiguous nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acid sequences of the embodiments will be constructed such that the open reading frame is maintained. For polynucleotides, conservative variants include those sequences that, because of the degeneracy of the genetic code, encode the amino acid sequence of one of the antifungal polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an antifungal protein of the embodiments. Generally, variants of a particular polynucleotide of the embodiments will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptides of SEQ ID NOs: 1, 3, 5, 7, and 9 are disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, antifungal activity as described herein. Such variants may result from, for example, genetic polymorphism or from human manipulation. Biologically active variants of a native antifungal protein of the embodiments will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the embodiments may differ from that protein by as few as 1-15 amino acid residues, as few as 1-10, such as 6-10, as few as 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the antifungal proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, Proteins (1984)).

Thus, the genes and polynucleotides of the embodiments include both the naturally occurring sequences as well as mutant forms. Likewise, the proteins of the embodiments encompass naturally occurring proteins as well as variations and modified forms thereof. Such variants will continue to possess the desired antifungal activity. Obviously, the mutations that will be made in the DNA encoding the variant must not place the sequence out of reading frame and optimally will not create complementary regions that could produce secondary mRNA structure. See, EP Patent No. 0075444.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular localization signals. "Pre" in this nomenclature generally refers to the signal peptide. The form of the translation product with only the signal peptide removed but no further processing yet is called a "propeptide" or "proprotein." The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that measure antifungal activity such as, for example, antifungal plate assays and other methods described elsewhere in this disclosure. See, for example, Duvick et al. (1992) *J. Biol. Chem.* 267:18841-18820, herein incorporated by reference.

Variant polynucleotides and proteins also encompass sequences and proteins derived from a mutagenic and recombinogenic procedure such as DNA shuffling. With such a procedure, one or more different antifungal protein coding sequences can be manipulated to create a new antifungal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the gene encoding an antifungal protein of the embodiments and other known genes encoding antifungal proteins to obtain a new gene coding for a protein with an improved property of interest, such as increased antifungal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an antifungal protein and which hybridize under stringent conditions to the sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to; methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the polynucleotides of the embodiments. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique among antifungal polynucleotide sequences and are optimally at least about 10 nucleotides in length, and most optimally at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. supra).

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acid sequences is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. supra.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See, for example ncbi.nlm.nih.gov on the World Wide Web by prefacing the provided internet address with the www prefix. Alignment may also be performed manually by inspection.

Unless otherwise stated, sequence identity/similarity values provided herein refer to the value obtained using GAP Version 10 using the following parameters: % identity and % similarity for a nucleotide sequence using Gap Weight of 50 and Length Weight of 3, and the nwsgapdna.cmp scoring matrix; % identity and % similarity for an amino acid sequence using Gap Weight of 8 and Length Weight of 2, and the BLOSUM62 scoring matrix; or any equivalent program thereof. "Equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the embodiments to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, but not limited to, single-stranded forms, double-stranded forms, and the like.

In some embodiments, expression cassettes comprising a promoter operably linked to a heterologous nucleotide sequence of the embodiments that encodes an antifungal polypeptide are further provided. The expression cassettes of the embodiments find use in generating transformed plants, plant cells, and microorganisms and in practicing the methods for inducing fungal pathogen resistance disclosed herein. The expression cassette will include 5' and 3' regulatory sequences operably linked to a polynucleotide of the embodiments. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked it is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antifungal polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the embodiments, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids*

Res. 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995)*Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, glyphosate and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724; and WO 02/36782. Such disclosures are herein incorporated by reference.

The above list of selectable marker genes is not meant to be limiting. Any selectable marker gene can be used in the embodiments.

The term "promoter" refers to regions or sequence located upstream and/or downstream from the start of transcription that are involved in recognition and binding of RNA polymerase and other proteins to initiate transcription. Promoters include nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A number of promoters can be used in the practice of the embodiments, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acid molecules can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell*

2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386; and the references cited therein. A further example is the inducible promoter for the maize PRms gene, whose expression is induced by the pathogen *Fusarium verticillioides* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the embodiments. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the antifungal polypeptides of the embodiments within a particular plant tissue. For example, a tissue-preferred promoter may be used to express an antifungal polypeptide in a plant tissue where disease resistance is particularly important, such as, for example, the roots, stems or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112 (3):1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, but are not limited to, the *Prunus serotina* prunasin hydrolase gene promoter (see, e.g., International Publication No. WO 03/006651), and also those found in U.S. patent application Ser. No. 10/109,488.

Stalk-preferred promoters may be used to drive expression of an antifungal polypeptide of the embodiments. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. Leach and Aoyagi (1991) describe their analysis of the promoters of the highly expressed rolC and rolD root-inducing genes of *Agrobacterium rhizogenes* (see *Plant Science* (Limerick) 79(1):69-76). Additional root-preferred promoters include the VfENOD-GRP3 gene promoter (Kuster et al. (1995) *Plant Mol. Biol.* 29(4):759-772); and rolB promoter (Capana et al. (1994)

*Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

In certain embodiments the nucleic acid sequences of the embodiments can be stacked with any combination of polynucleotide sequences of interest in order to create plants with a desired phenotype. For example, the polynucleotides of the embodiments may be stacked with any other polynucleotides of the embodiments, such as any combination of SEQ ID NOS: 3, 6, 9, 12, 13, or 14, or with other antifungal genes and the like. The combinations generated can also include multiple copies of any one of the polynucleotides of interest. The polynucleotides of the embodiments can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxic proteins (U.S. Pat. Nos. 5,366,892; 5,747,450; 5,737,514; 5723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The methods of the embodiments involve introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the embodiments do not depend on a particular method for introducing a sequence into a plant, only that the polynucleotide gains access to the interior of at least one cell of the plant. Methods for introducing polynucleotides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) Plant Cell *Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the antifungal sequences of the embodiments can be provided to a plant using a variety of transient transformation methods. Such transient transformation methods include, but are not limited to, the introduction of the antifungal protein or variants and fragments thereof directly into the plant or the introduction of the antifungal protein transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include a viral vector system and the precipitation of the polynucleotide in a manner that precludes subsequent release of the DNA. Thus, the transcription from the particle-bound DNA can occur, but the frequency with which its released to become integrated into the genome is greatly reduced. Such methods include the use of particles coated with polyethylimine (PEI; Sigma #P3143).

In other embodiments, the polynucleotides of the embodiments may be introduced into plants by contacting plants with a virus or viral nucleic acids. Generally, such methods involve incorporating a nucleotide construct of the embodiments within a viral DNA or RNA molecule. It is recognized that the antifungal polypeptide of the embodiments may be initially synthesized as part of a viral polyprotein, which later may be processed by proteolysis in vivo or in vitro to produce the desired recombinant protein. Further, it is recognized that promoters of the embodiments also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provide transformed seed (also referred to as "transgenic seed") having a nucleotide construct of the embodiments, for example, an expression cassette of the embodiments, stably incorporated into their genome.

As used herein, the term "plant" includes whole plants, plant cells, plant protoplasts, plant cell tissue cultures from which a maize plant can be regenerated, plant calli, plant clumps, and plant cells that are intact in plants or parts of plants such as embryos, pollen, seeds, endosperm, seed coat, leaves, flowers, floral organs/structures (e.g. bracts, sepals, petals, stamens, carpels, anthers and ovules) branches, fruit, kernels, ears, cobs, husks, stalks, tubers, roots, root tips, anthers, plant tissue (e.g. vascular tissue, ground tissue, and the like) and cells (e.g. guard cells, egg cells, trichomes and the like) and progeny of same. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides. The class of plants that can be used in the method of the embodiments is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The methods of the embodiments may be used to induce fungal resistance in, or protect from fungal pathogen attack any plant species, including, but not limited to, monocots and dicots. Examples of plant species of interest include, but are not limited to, corn (*Zea mays*), *Brassica* sp. (e.g., *B. napus*, *B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon lycopersicon*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the embodiments are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Antifungal compositions are also encompassed by the present invention. Antifungal compositions may comprise antifungal polypeptides or transformed microorganisms comprising a nucleotide sequence that encodes an antifungal polypeptide. The antifungal compositions of the invention may be applied to the environment of a plant fungal pathogen, as described herein below, thereby protecting a plant from fungal pathogen attack. Moreover, an antifungal composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

A gene encoding an antifungal polypeptide of the embodiments may be introduced into any suitable microbial host according to standard methods in the art. For example, microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, and to provide for stable maintenance and expression of the gene expressing the antifungal protein.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

Other illustrative prokaryotes, both Gram-negative and gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

Genes encoding the antifungal proteins of the embodiments can be introduced into microorganisms that multiply on plants (epiphytes) to deliver antifungal proteins to potential target fungal pathogens. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the antifungal polypeptides of the embodiments can be introduced into a root-colonizing *Bacillus cereus* by standard methods known in the art.

Genes encoding antifungal proteins can be introduced, for example, into the root-colonizing *Bacillus* by means of electrotransformation. Specifically, genes encoding the proteins can be cloned into a shuttle vector, for example, pHT3101 (Lerecius et al. (1989) *FEMS Microbiol. Letts.* 60: 211-218. The shuttle vector pHT3101 containing the coding sequence for the particular protein can, for example, be transformed into the root-colonizing *Bacillus* by means of electroporation (Lerecius et al. (1989) *FEMS Microbiol. Letts.* 60: 211-218).

Methods are provided for protecting a plant from a fungal pathogen comprising applying an effective amount of an antifungal protein or composition of the invention to the environment of the fungal pathogen. "Effective amount" is intended to mean an amount of a protein or composition sufficient to control a pathogen. The antifungal proteins and compositions can be applied to the environment of the pathogen by methods known to those of ordinary skill in the art.

The antifungal compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the antifungal proteins of the present invention include, but are not limited to, foliar application, seed coating, and soil application. The number of applications and the rate of application depend on the intensity of infestation by the corresponding fungal pathogen.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The antifungal compositions of the present invention can be in a suitable form for direct application or as a concentrate of primary composition that requires dilution with a suitable quantity of water or other diluent before application. The concentration of the antifungal polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

In a further embodiment, the compositions, as well as the transformed microorganisms and antifungal proteins, of the invention can be treated prior to formulation to prolong the antifungal activity when applied to the environment of a target pathogen as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The antifungal compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. For example, the antifungal protein and/or transformed microorganisms of the invention may be mixed with grain to protect the grain during storage. It is generally important to obtain good control of pathogens in the early stages of plant growth, as this is the time when the plant can be most severely damaged. The compositions of the invention can conveniently contain an insecticide if this is thought necessary. The composition may be applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, an inert carrier, and dead cells of a *Bacillus* strain or transformed microorganism of the invention.

Compositions of the invention find use in protecting plants, seeds, and plant products in a variety of ways. For example, the compositions can be used in a method that involves placing an effective amount of the antifungal composition in the environment of the pathogen by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protective coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by fungal pathogens. In order to treat the seed, the protective coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a DNA molecule comprising a nucleotide sequence encoding an antifungal polypeptide of the invention may be treated with a seed protective coating comprising a seed treatment compound, such as, for example, captan, carboxin, thiram, methalaxyl, pirimiphos-methyl, and others that are commonly used in seed treatment. Alternatively, a seed of the invention comprises a seed protective coating comprising an antifungal composition of the invention is used alone or in combination with one of the seed protective coatings customarily used in seed treatment.

The antifungal polypeptides of the invention can be used for any application including coating surfaces to target microbes. In this manner, the target microbes include human pathogens or microorganisms. Surfaces that might be coated with the antifungal polypeptides of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047, herein incorporated by reference.

The methods of the embodiments may be effective against a variety of plant fungal pathogens, such as, but not limited to, *Colletotrichum graminocola, Diplodia maydis, Verticillium dahliae, Fusarium graminearum, Fusarium oxysporum* and *Fusarium verticillioides*. Specific pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata, Glomerella glycines, Phakopsora pachyrhizi, Pythium aphanidermatum, Pythium ultimum, Pythium debaryanum, Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana, Claviceps purpurea, Tilletia tritici, Tilletia laevis, Ustilago tritici, Tilletia* indica, *Rhizoctonia solani, Pythium arrhenomannes, Pythium gramicola, Pythium aphanidermatum*, Sunflower: *Plasmopora halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium verticillioides* var. *subglutinans, Erwinia stewartii, F. verticillioides, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride, Claviceps sorghi, Pseudomonas avenae, Erwinia chrysanthemi* pv. *zea, Erwinia carotovora*, Corn stunt spiroplasma, *Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Sorghum: *Exserohilum turcicum, C. sublineolum, Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium verticillioides, Alternaria alternata, Bipolaris sorghicola, Helminthosporium sorghicola, *Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola,* etc.

The article "a" and "an" are used herein to refer to one or more than one (i.e., to at least one) of the grammatical object of the article. By way of example, "an element" means one or more element.

Units, prefixes, and symbols may be denoted in their Si accepted form. Unless otherwise indicated, nucleic acid sequences are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXPERIMENTAL

Example 1

Antifungal Bioassays

A number of defensin polypeptides were recombinantly expressed in *E. coli* and then screened in an antifungal bioassay. Expression of biologically functional polypeptides involved producing a fusion protein that included a maltose-binding protein (MBP) and a polypeptide of interest and subsequently cleaving the fusion protein at a protease recognition sequence to release the peptide of interest. DNA encoding the polypeptide of interest was fused to the C-terminus of the MeIE gene in the *E. coli* expression vector PMAL (New England Biolabs; see, Guan et al., *Gene* 67:21-30 (1987); and Maina et al., *Gene* 74:365-73 (1988)). Sequences encoding the cleavage site of proteases Factor Xa or Genenase I were incorporated between the genes of MBP and the polypeptide of interest. A histidine tag was also added to the N-terminus of MBP.

The constructed plasmid vector was transformed into cells of *E. coli* XL-1 Blue and transformants were grown in 2YT medium containing 50 µg/ml carbenicillin to a cell density of $O.D._{600}=0.6$-$0.9$. Expression of the fusion protein was induced by addition of IPTG into the culture to a final concentration of 1 mM. Cells were grown for 4-16 hours to saturation before harvesting. Cells were harvested by centrifugation and then lysed with B-PER reagent (Pierce Chemicals, Rockford, Ill.) to obtain the fraction of soluble proteins. The fusion protein was purified from the cell lysate supernatant utilizing the histidine tag by incubating the cell lysate with Ni-NTA agarose resins for 20 minutes to 1 hour. The resins were washed with Tris buffer to remove all unbound proteins. Two-mercaptoethanol (10 mM) was included in the lysis and washing buffers to allow partial refolding of the proteins. Elution of the bound fusion protein was performed with buffer containing 20-40 mM histidine. To release the polypeptide of interest, the purified fusion protein was incubated with Factor Xa or Genease I (RT, 8-24 h). The cleaved protein sample was then used in antifungal activity assays.

All fungal strains were grown and maintained on potato dextrose agar (PDA) plates, in a 30° C. incubator. These plates were kept in smaller secondary containers (per fungal strain), with moist paper towels to maintain high humidity. Spores were harvested in a quarter strength of potato dextrose broth (PDB) after about 2 weeks of growth, counted using a hemacytometer, and subsequently stored in small aliquots at −80° C.

The frozen spores were diluted to the working concentration (determined empirically for each fungal strain), in a quarter strength of PDB, and 50 µL (per well) were added to sterile, flat-bottomed 96-well assay plates. The assay plates were incubated in the humid boxes at room temperature for 5-7 hours to allow the spores to germinate. Serial dilutions of purified, protease-cleaved fusion protein samples were then added to the assay plates, in 50 µL volumes, for a final assay volume of 100 µL per well. The assay plates were allowed to incubate overnight, in a humid box, at 30° C. Antifungal activity was scored after 18 to 48 hours, depending upon the strain of fungus.

Table 1 illustrates those polypeptides identified to have activity against at least one of the listed fungal pathogens.

TABLE 1

Primary screening
(score: 0 = no effect; 1 = partial growth inhibition; 2 = strong inhibition):

|       | SEQ ID NO: | *Alternaria brassicicola* | *Fusarium verticillioides* | *Fusarium oxysporum* | *Botrytis cinerea* | *Verticillium dahliae* |
|-------|------------|---------------------------|----------------------------|----------------------|--------------------|------------------------|
| Dfn2  | 2          | 0                         | 1                          | 1                    | 0                  | 2                      |
| Dfn4  | 5          | 0                         | 1                          | 1                    | 0                  | 2                      |
| Dfn7  | 8          | 0                         | 0                          | 0                    | 0                  | 1                      |
| Dfn9  | 11         | 0                         | 0                          | 0                    | 0                  | 2                      |
| Dfn13 | 14         | 0                         | 0                          | 0                    | 0                  | 1                      |
| Dfn14 | 17         | 1                         | 0                          | 0                    | 1                  | 0                      |
| Dfn16 | 20         | 0                         | 0                          | 1                    | 0                  | 0                      |
| Dfn25 | 23         | 0                         | 0                          | 1                    | 0                  | 1                      |

TABLE 1-continued

Primary screening
(score: 0 = no effect; 1 = partial growth inhibition; 2 = strong inhibition):

| | SEQ ID NO: | Alternaria brassicicola | Fusarium verticillioides | Fusarium oxysporum | Botrytis cinerea | Verticillium dahliae |
|---|---|---|---|---|---|---|
| Dfn26 | 26 | 0 | 0 | 1 | 0 | 0 |
| Dfn50 | 35 | 0 | 0 | 1 | 0 | 2 |

A number of other defensin sequences were tested against the five fungal strains for antifungal activity. The sequences presented in SEQ ID NOs: 31-78 were similarly tested but did not show activity against these five fungal pathogens. This does not mean that the defensins set forth in SEQ ID NOs: 31-78 do not possess any antifungal activity, but merely that they do not show activity against the five fungi tested. It is likely that these defensins would show antifungal activity against other fungal targets.

Example 2

Transformation and Regeneration of Transgenic Maize Plants

Immature maize embryos from greenhouse donor plants are bombarded with a plasmid containing a nucleotide sequence encoding the antifungal polypeptide set forth in SEQ ID NO: 1 operably linked to a promoter that drives expression in a maize plant cell and a selectable marker (e.g., the selectable marker gene PAT (Wohlleben et al. (1988) *Gene* 70:25-37), which confers resistance to the herbicide Bialaphos). Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence encoding the antifungal polypeptide set forth in SEQ ID NO: 1 operably linked to a promoter that drives expression in a maize cell is made. This plasmid DNA plus plasmid DNA containing a selectable marker (e.g., PAT) is precipitated onto 1.1 μm (average diameter) tungsten pellets using a $CaCl_2$ precipitation procedure as follows:

100 μL prepared tungsten particles in water
10 μL (1 μg) DNA in Tris EDTA buffer (1 μg total DNA)
100 μL 2.5 M $CaCl_2$
10 μL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for fungal resistance.

Bombardment and Culture Media

Bombardment medium (560Y) comprises 4.0 g/L N6 basal salts (SIGMA C-1416), 1.0 mL/L Eriksson's Vitamin Mix (1000× SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000×SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I H₂O); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I H₂O), 0.1 g/L myo-inositol, and 40.0 g/L sucrose (brought to volume with polished D-I H₂O after adjusting pH to 5.6); and 6 g/L bacto-agar (added after bringing to volume with polished D-I H₂O), sterilized and cooled to 60° C.

Example 3

Agrobacterium-mediated Transformation of Maize and Regeneration of Transgenic Plants For Agrobacterium-mediated transformation of maize with the polynucleotide construct containing SEQ ID NO: 1, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the polynucleotide construct to at least one cell of at least one of the immature embryos (step 1: the infection step). In this step the immature embryos are immersed in an Agrobacterium suspension for the initiation of inoculation. The embryos are co-cultured for a time with the Agrobacterium (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of Agrobacterium without the addition of a selective agent for plant transformants (step 3: resting step). The immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 4

Transformation of Somatic Soybean Embryo Cultures and Regeneration of Soybean Plants The following stock solutions and media are used for transformation and regeneration of soybean plants:

Stock Solutions

Sulfate 100× Stock: 37.0 g MgSO₄.7H₂O, 1.69 g MnSO₄.H₂O, 0.86 g ZnSO₄.7H₂O, 0.0025 g CuSO₄.5H₂O.

Halides 100× Stock: 30.0 g CaCl₂.2H₂O, 0.083 g KI, 0.0025 g CoCl₂.6H₂O,

P, B, Mo 100× Stock: 18.5 g KH₂PO₄, 0.62 g H₃BO₃, 0.025 g Na₂MoO₄.2H₂O

Fe EDTA 100× Stock: 3.724 g Na₂EDTA, 2.784 g FeSO₄.7H₂O.

2,4-D Stock: 10 mg/mL.

Vitamin B5 1000× Stock: 10.0 g myo-inositol, 0.10 g nicotinic acid, 0.10 g pyridoxine HCl, 1 g thiamine.

Media (per Liter)

SB196: 10 mL of each of the above stock solutions, 1 mL B5 vitamin stock, 0.463 g (NH₄)₂ SO₄, 2.83 g KNO₃, 1 mL 2,4-D stock, 1 g asparagine, 10 g sucrose, pH 5.7.

SB103: 1 pk. Murashige & Skoog salts mixture, 1 mL B5 vitamin stock, 750 mg MgCl₂ hexahydrate, 60 g maltose, 2 g gelrite, pH 5.7.

SB166: SB103 supplemented with 5 g per liter activated charcoal.

SB71-4: Gamborg's B5 salts (Gibco-BRL catalog No. 21153-028), 1 mL B5 vitamin stock, 30 g sucrose, 5 g TC agar, pH 5.7.

Soybean embryogenic suspension cultures are maintained in 35 mL liquid medium (SB196) on a rotary shaker (150 rpm) at 28° C. with fluorescent lights providing a 16 hour day/8 hour night cycle. Cultures are subcultured every 2 weeks by inoculating approximately 35 mg of tissue into 35 mL of fresh liquid media.

Soybean embryogenic suspension cultures are transformed by the method of particle gun bombardment (see Klein et al. (1987) Nature 327:70-73) using a DuPont Biolistic PDS1000/He instrument.

In particle gun bombardment procedures it is possible to use purified 1) entire plasmid DNA or, 2) DNA fragments containing only the recombinant DNA expression cassette(s) of interest. For every eight bombardment transformations, 30 μl of suspension is prepared containing 1 to 90 picograms (pg) of DNA fragment per base pair of DNA fragment. The recombinant DNA plasmid or fragment used to express the antifungal gene is on a separate recombinant DNA plasmid or fragment from the selectable marker gene. Both recombinant DNA plasmids or fragments are co-precipitated onto gold particles as follows. The DNAs in suspension are added to 50 μL of a 20-60 mg/mL 0.6 μm gold particle suspension and then combined with 50 μL CaCl₂ (2.5 M) and 20 μL spermidine (0.1 M) The mixture is pulse vortexed 5 times, spun in a microfuge for 10 seconds, and the supernatant removed. The DNA-coated particles are then washed once with 150 μL of 100% ethanol, pulse vortexed and spun in a microfuge again, and resuspended in 85 μL of anhydrous ethanol. Five μL of the DNA-coated gold particles are then loaded on each macrocarrier disk.

Approximately 150 to 250 mg of two-week-old suspension culture is placed in an empty 60 mm×15 mm petri plate and the residual liquid is removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Eighteen plates are bombarded, and, following bombardment, the tissue from each plate is divided between two flasks, placed back into liquid media, and cultured as described above.

Seven days after bombardment, the liquid medium is exchanged with fresh SB196 medium supplemented with 50 mg/mL hygromycin or 100 ng/mL chlorsulfuron, depending on the selectable marker gene used in transformation. The selective medium is refreshed weekly or biweekly. Seven weeks post-bombardment, green, transformed tissue is observed growing from untransformed, necrotic embryogenic clusters. Isolated green tissue is removed and inoculated into individual flasks to generate new, clonally-propagated, transformed embryogenic suspension cultures. Thus, each new line is treated as independent transformation event.

These suspensions can then be maintained as suspensions of embryos clustered in an immature developmental stage through subculture or can be regenerated into whole plants by maturation and germination of individual somatic embryos.

Transformed embryogenic clusters are removed from liquid culture and placed on solid agar medium (SB166) containing no hormones or antibiotics for one week. Embryos are cultured at 26° C. with mixed fluorescent and incandescent lights on a 16 hour day: 8 hour night schedule. After one week, the cultures are then transferred to SB103 medium and maintained in the same growth conditions for 3 additional weeks. Prior to transfer from liquid culture to solid medium, tissue from selected lines is assayed by PCR or Southern analysis for the presence of the antifungal gene.

Somatic embryos become suitable for germination after 4 weeks and are then removed from the maturation medium and dried in empty petri dishes for 1 to 5 days. The dried embryos are then planted in SB71-4 medium where they are allowed to germinate under the same light and germination conditions described above. Germinated embryos are transferred to sterile soil and grown to maturity.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for enhancing resistance of a plant to a pathogen, said method comprising:
   (a) stably transforming a plant cell with at least one expression cassette comprising a nucleotide sequence operably linked to a promoter that drives expression in a cell of said plant, wherein said nucleotide sequence has at least 95% sequence identity to SEQ ID NO: 12, and further wherein said nucleotide sequence encodes a polypeptide having activity against at least one plant fungal pathogen; and
   (b) regenerating a transformed plant from said plant cell, wherein the level of resistance to said fungal pathogen in said plant is increased in comparison to a plant that does not comprise said expression cassette.

2. The method of claim 1, wherein the promoter is selected from the group consisting of:
   a) a constitutive promoter;
   b) a tissue-specific promoter; and
   c) an inducible promoter.

3. The method of claim 1, wherein the polypeptide further comprises a heterologous signal sequence.

4. The method of claim 3, wherein the signal sequence is a secretion signal sequence.

5. The method of claim 3, wherein the signal sequence is an organelle signal sequence.

6. The method of claim 3, wherein the signal sequence is a plastid signal sequence.

7. The method of claim 1, wherein the nucleotide sequence is SEQ ID NO: 12.

8. A transgenic plant having stably incorporated into its genome a polynucleotide sequence at least 95% identical to SEQ ID NO: 12, wherein said polynucleotide sequence encodes a polypeptide with activity against plant fungal pathogens, further wherein said plant has improved fungal pathogen resistance to at least one plant pathogenic fungus.

9. The plant according to claim 8, wherein said plant is a monocot.

10. The plant according to claim 8, wherein said plant is a dicot.

11. Transformed seed of the plant of claim 8, wherein the seed comprise the polynucleotide sequence.

12. The plant according to claim 8, wherein said polynucleotide is operably linked to a promoter that drives expression in a cell of said plant, wherein said promoter is selected from the group consisting of:
   a) a constitutive promoter;
   b) a tissue-specific promoter; and
   c) an inducible promoter.

13. The plant according to claim 8, wherein the polypeptide further comprises a heterologous signal sequence.

14. The plant according to claim 13, wherein the signal sequence is a secretion signal sequence.

15. The plant according to claim 13, wherein the signal sequence is an organelle signal sequence.

16. The plant according to claim 13, wherein the signal sequence is a plastid signal sequence.

17. The plant according to claim 8, wherein said polynucleotide sequence is SEQ ID NO: 12.

18. The method of claim 2, wherein the tissue-specific promoter is a root-specific promoter, and the inducible promoter is a pathogen-inducible promoter.

19. The plant of claim 12, wherein the tissue-specific promoter is a root-specific promoter, and the inducible promoter is a pathogen-inducible promoter.

* * * * *